(12) United States Patent
Ohtsuka et al.

(10) Patent No.: US 12,310,564 B2
(45) Date of Patent: May 27, 2025

(54) INTRAORAL CAMERA SYSTEM AND IMAGE DISPLAY METHOD

(71) Applicant: Panasonic Intellectual Property Management Co., Ltd., Osaka (JP)

(72) Inventors: Yoshio Ohtsuka, Osaka (JP); Masato Izawa, Osaka (JP); Tomoki Ogawa, Osaka (JP); Toshiyuki Nakashima, Nara (JP); Masayuki Aihara, Osaka (JP); Kazuhiro Funamoto, Hyogo (JP); Tadashi Miki, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 455 days.

(21) Appl. No.: 17/921,289

(22) PCT Filed: Feb. 17, 2022

(86) PCT No.: PCT/JP2022/006364
§ 371 (c)(1),
(2) Date: Oct. 25, 2022

(87) PCT Pub. No.: WO2022/176943
PCT Pub. Date: Aug. 25, 2022

(65) Prior Publication Data
US 2023/0165454 A1    Jun. 1, 2023

(30) Foreign Application Priority Data
Feb. 22, 2021    (JP) .................................. 2021-026041

(51) Int. Cl.
*A61B 1/247*    (2006.01)
*A61B 1/00*    (2006.01)
(Continued)

(52) U.S. Cl.
CPC .......... *A61B 1/247* (2013.01); *A61B 1/00009* (2013.01); *A61B 1/00045* (2013.01);
(Continued)

(58) Field of Classification Search
CPC . A61B 1/247; A61B 1/00009; A61B 1/00045; A61B 1/04; A61B 2562/0219;
(Continued)

(56) References Cited

U.S. PATENT DOCUMENTS 5,661,519 A * 8/1997 Franetzki ........... A61B 1/00183
348/66
9,463,081 B2 * 10/2016 Urakabe ................ A61C 19/04
(Continued)

FOREIGN PATENT DOCUMENTS

JP    2018-534086 A    11/2018
JP    2019-141582 A    8/2019
(Continued)

OTHER PUBLICATIONS

Extended European Search Report dated Jul. 17, 2024 issued in the corresponding European Patent Application No. 22756261.8.
(Continued)

*Primary Examiner* — Timothy R Newlin
(74) *Attorney, Agent, or Firm* — Rimon P.C.

(57) ABSTRACT

An intraoral camera system includes an imaging unit and an image processor. If a first angle formed by an imaging plane perpendicular to the optical axis of the imaging unit and a first direction that is the vertically upward direction along a vertical axis is less than a predetermined second angle, the image processor rotates image data to cause the vertically upward direction along the vertical axis to coincide with an upward direction of an image by rotating the image data by a third angle formed by the first direction and a second direction from a handle toward a head.

11 Claims, 19 Drawing Sheets

(51) Int. Cl.
*A61B 1/04* (2006.01)
*A61C 19/04* (2006.01)
*G06T 3/60* (2006.01)

(52) U.S. Cl.
CPC ........ *A61B 1/04* (2013.01); *A61B 2562/0219* (2013.01); *A61C 19/04* (2013.01); *G06T 3/60* (2013.01)

(58) Field of Classification Search
CPC ........ A61B 1/000094; A61B 1/000095; A61B 1/0005; A61C 19/04; A61C 9/0053; G06T 3/60
See application file for complete search history.

(56) References Cited

U.S. PATENT DOCUMENTS

| | | | |
|---|---|---|---|
| 10,231,611 | B2 | 3/2019 | Li |
| 10,362,240 | B2* | 7/2019 | Richardson ............ H04N 23/54 |
| 11,497,382 | B1* | 11/2022 | Ikuta .................. A61B 1/00096 |
| 2002/0161280 | A1* | 10/2002 | Chatenever ............ A61B 1/042 600/137 |
| 2005/0123179 | A1* | 6/2005 | Chen ........................ G06T 3/60 382/128 |
| 2010/0168516 | A1* | 7/2010 | Uchiyama .......... A61B 1/00045 600/117 |
| 2014/0036050 | A1* | 2/2014 | Yoshino ................. H04N 25/61 348/65 |
| 2014/0342301 | A1* | 11/2014 | Fleer ..................... A61B 5/0088 433/102 |
| 2015/0250380 | A1* | 9/2015 | Ikeda ................. A61B 1/00133 600/111 |
| 2017/0135563 | A1* | 5/2017 | Uemori .............. A61B 1/00045 |
| 2019/0069766 | A1* | 3/2019 | Mizukura .......... A61B 1/00045 |
| 2020/0305702 | A1 | 10/2020 | Yoshikawa et al. |
| 2021/0152806 | A1* | 5/2021 | Babayoff ............... G01J 3/0256 |
| 2022/0222787 | A1* | 7/2022 | Couade ................... G06T 7/269 |
| 2022/0392110 | A1* | 12/2022 | De Almeida Barreto ................... A61B 1/0005 |

FOREIGN PATENT DOCUMENTS

| | | |
|---|---|---|
| WO | 2012/096312 A1 | 7/2012 |
| WO | 2019/065700 A1 | 4/2019 |

OTHER PUBLICATIONS

International Search Report issued on May 10, 2022 in International Patent Application No. PCT/JP2022/006364, with English translation.

* cited by examiner

INTRAORAL CAMERA SYSTEM AND IMAGE DISPLAY METHOD

CROSS-REFERENCE OF RELATED APPLICATIONS

This application is the U.S. National Phase under 35 U.S.C. § 371 of International Patent Application No. PCT/JP2022/006364, filed on Feb. 17, 2022, which in turn claims the benefit of Japanese Patent Application No. 2021-026041, filed on Feb. 22, 2021, the entire disclosures of which Applications are incorporated by reference herein.

TECHNICAL FIELD

The present disclosure relates to an intraoral camera system and an image display method.

BACKGROUND ART

Patent Literature 1 (PTL 1) discloses an intraoral camera system that captures an image of teeth inside a mouth.

CITATION LIST

Patent Literature

[PTL 1] Japanese Unexamined Patent Application Publication No. 2019-141582

SUMMARY OF INVENTION

Technical Problem

Such intraoral camera systems are hoped to properly display a captured tooth image.

Thus, the present disclosure aims to provide an intraoral camera system and an image display method that are capable of properly displaying a captured tooth image.

Solution to Problem

An intraoral camera system according to one aspect of the present disclosure includes an imaging unit, a sensor, an image processor, and a display. The imaging unit includes a handle, a head, and a neck and captures an image of a tooth inside a mouth to generate image data, the head including an image sensor that generates the image data, and the neck connecting the handle to the head. The sensor detects the orientation of the imaging unit. The image processor performs image processing for the image data according to the orientation of the imaging unit detected by the sensor. The display displays the image data that has undergone the image processing. If a first angle formed by an imaging plane perpendicular to the optical axis of the imaging unit and a first direction that is the vertically upward direction along a vertical axis is less than a predetermined second angle, the image processor rotates the image data to cause the vertically upward direction along the vertical axis to coincide with the upward direction of an image by rotating the image data by a third angle formed by the first direction and a second direction from the handle toward the head.

Advantageous Effects of Invention

The present disclosure provides an intraoral camera system and an image display method that are capable of properly displaying a captured tooth image.

DESCRIPTION OF EMBODIMENTS

Figure 1:
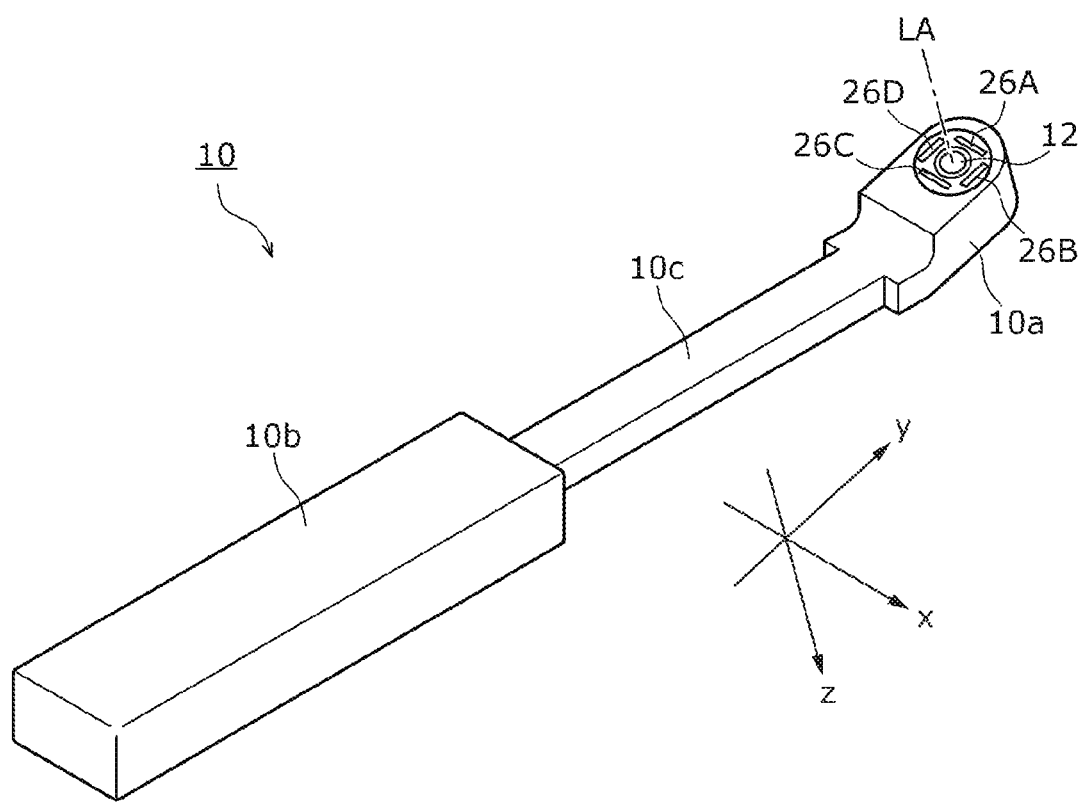
FIG. 1 is a perspective view of the intraoral camera of an intraoral camera system according to an embodiment.

An intraoral camera system according to one aspect of the present disclosure includes an imaging unit, a sensor, an image processor, and a display. The imaging unit includes a handle, a head, and a neck and captures an image of a tooth inside a mouth to generate image data, the head including an image sensor that generates the image data, and the neck connecting the handle to the head. The sensor detects the orientation of the imaging unit. The image processor performs image processing for the image data according to the orientation of the imaging unit detected by the sensor. The display displays the image data that has undergone the image processing. If a first angle formed by an imaging plane perpendicular to the optical axis of the imaging unit and a first direction that is the vertically upward direction along a vertical axis is less than a predetermined second angle, the image processor rotates the image data to cause the vertically upward direction along the vertical axis to coincide with the upward direction of an image by rotating the image data by a third angle formed by the first direction and a second direction from the handle toward the head.

Thus, the intraoral camera system can properly display the captured tooth image. For instance, a user can check the image reflecting the real vertical positional relationship. Accordingly, the user can intuitively understand their tooth condition.

For instance, if the first angle is greater than or equal to the second angle, the image processor may rotate the image data to cause a portion of the image data corresponding to the head side of the imaging unit to appear at a top portion of an image.

For instance, if the first angle is less than the second angle, the image processor may display, on the display, information notifying that an image being displayed on the display is an image of the side surface of a tooth captured inside the mouth of the user by the imaging unit. If the first angle is greater than or equal to the second angle, the image processor may display, on the display, information notifying that an image being displayed on the display is an image of the top of a tooth captured inside the mouth of the user by the imaging unit.

In this way, the intraoral camera system displays the direction in which the tooth image is captured. Thus, the user can readily identify the direction in which the tooth image is currently being captured, which can improve user convenience.

For instance, if a difference between the first angle and the second angle is less than a predetermined value, the image processor may detect, from the image data, a tooth area and a gum area extending along the tooth area. If the gum area is detected on both the buccal side and the lingual side of the tooth area, the image processor may rotate the image data to cause a portion of the image data corresponding to the head side of the imaging unit to appear at a top portion of an image. If the gum area is detected only on one of the buccal side and the lingual side of the tooth area, the image processor may calculate the cosine of a fourth angle formed by the first direction and a third direction that is the direction from the imaging unit toward a subject along the optical axis of the imaging unit. If the value of the cosine calculated is positive, the image processor may rotate the image data to cause the tooth area to be below the gum area in the image data. If the value of the cosine calculated is negative, the image processor may rotate the image data to cause the tooth area to be above the gum area in the image data.

Thus, if the first angle is close to the second angle, the intraoral camera system rotates the image data according to the relationship between the gum area and the tooth area and the cosine of the fourth angle. Accordingly, the intraoral camera system can improve determination accuracy when the first angle is close to the second angle.

For instance, the image processor may further horizontally flip the image data, and the display may display the image data that has been rotated and horizontally flipped.

Thus, for instance, the user can check their teeth in the same state as their teeth are reflected on a mirror. Accordingly, the user can intuitively understand their tooth condition.

For instance, the image processor may further rotate the image data according to the orientation of the display.

Thus, for instance, the user can check the image reflecting the real vertical positional relationship. Accordingly, the user can intuitively understand their tooth condition.

For instance, the intraoral camera system may obtain an initial orientation that is a predetermined orientation of the imaging unit and adjust the first direction by using the initial orientation.

Thus, the intraoral camera system can improve the accuracy of the processing by adjusting the orientation of the imaging unit according the user's posture.

For instance, the predetermined orientation may be the orientation of the imaging unit when the posture of the user and the orientation of the imaging unit have a predetermined relationship.

For instance, in the predetermined orientation, the imaging plane of the imaging unit may be parallel to the frontal plane of the user, and the vertical axis of the user and the second direction may be identical or orthogonal when viewed in a direction perpendicular to the imaging plane.

For instance, in the predetermined orientation, a predetermined tooth and the imaging plane of the imaging unit may be parallel to and face each other, and the second direction and a height direction of the predetermined tooth may be identical or orthogonal when viewed in a direction perpendicular to the imaging plane.

Thus, the user can readily obtain the initial orientation. In addition, improvement in the accuracy of the initial orientation leads to improvement in the accuracy of adjustment.

An image display method according to another aspect includes capturing an image of a tooth inside a mouth to generate image data by an imaging unit that includes a handle, a head including an image sensor that generates the image data, and a neck connecting the handle to the head, detecting the orientation of the imaging unit, performing image processing for the image data according to the orientation of the imaging unit detected, and displaying the image data that has undergone the image processing. In the image processing, if a first angle formed by an imaging plane perpendicular to the optical axis of the imaging unit and a first direction that is the vertically upward direction along a vertical axis is less than a predetermined second angle, by rotating the image data by a third angle formed by the first direction and a second direction from the handle toward the head, the image data is rotated to cause the vertically upward direction along the vertical axis to coincide with the upward direction of an image.

Thus, in the image display method, it is possible to properly display a captured tooth image. For instance, the user can check the image reflecting the real vertical positional relationship. Accordingly, the user can intuitively understand their tooth condition.

It should be noted that these general or specific aspects may be embodied as a system, a method, an integrated circuit, a computer program, or a computer-readable recording medium, such as a CD-ROM, or may be embodied by any combination of the system, the method, the integrated circuit, the computer program, and the recording medium.

Hereinafter, an embodiment is described in detail with reference to appropriate drawings. However, excessively detailed explanations may be omitted. For instance, detailed explanations for well-known matters and overlapping explanations for substantially the same structural elements may be omitted. Such an omission is made to avoid unnecessary redundancy of the descriptions below and to facilitate understanding by those skilled in the art.

It should be noted that the inventors of the present disclosure provide the appended drawings and the following descriptions for thorough understanding of the present disclosure by those skilled in the art. There is no intention to limit the present disclosure by the appended drawings and the following descriptions.

Embodiment

FIG. 1 is a perspective view of the intraoral camera of an intraoral camera system according to the embodiment. As illustrated in FIG. 1, intraoral camera 10 includes a toothbrush-shaped case that can be handled by one hand. The case includes head 10a, handle 10b, and neck 10c. Head 10a is put inside a user's mouth when a dentition image is captured. Handle 10b is designed to be held by a user. Neck 10c connects head 10a to handle 10b.

Imaging optical system 12 is incorporated into head 10a and neck 10c. Imaging optical system 12 includes image sensor 14 and a lens (not illustrated in FIG. 1) disposed on optical axis LA.

Image sensor 14 is an image device, such as a C-MOS sensor or a CCD sensor, and the lens forms an image of a tooth. Image sensor 14 outputs a signal (image data) corresponding to the formed image to an external device.

In addition, intraoral camera 10 is equipped with first to fourth LEDs 26A to 26D as lighting devices that illuminate a target tooth during image capturing. First to fourth LEDs 26A to 26D are, for example, white LEDs.

Figure 2:
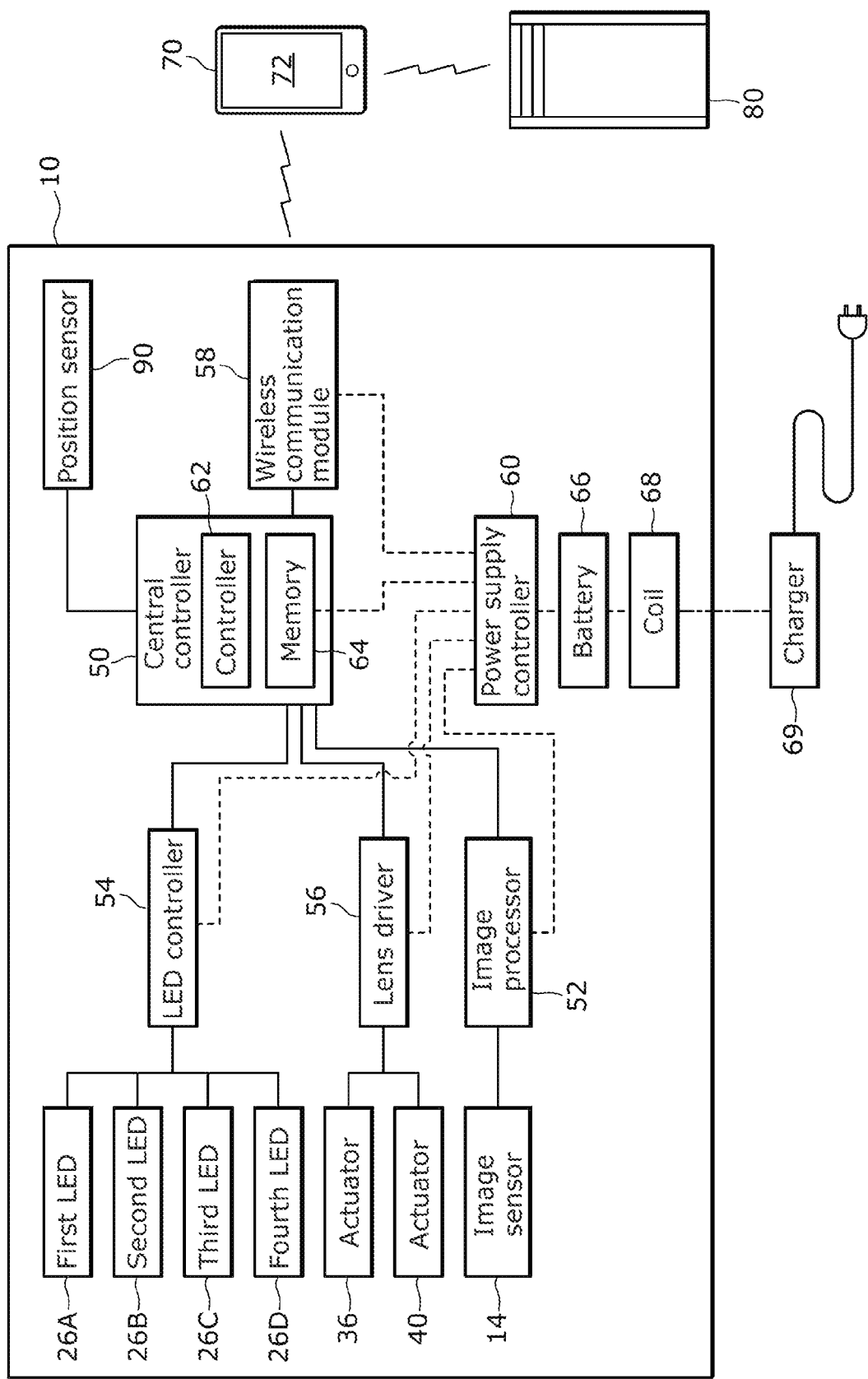
FIG. 2 illustrates a schematic configuration of the intraoral camera system according to the embodiment.

FIG. 2 is a schematic configuration of the intraoral camera system according to the embodiment. As illustrated in FIG. 2, in the overview of operation, the intraoral camera system according to the embodiment captures a dentition image by using intraoral camera 10 and performs image processing for the captured image.

As illustrated in FIG. 2, the intraoral camera system includes intraoral camera 10, portable terminal 70, and cloud server 80. Portable terminal 70 is, for example, a wirelessly communicable smartphone or a tablet terminal. Portable terminal 70 includes, as an input device and an output device, touch screen 72 capable of displaying, for example, a dentition image. Portable terminal 70 functions as a user interface of the intraoral camera system.

Cloud server 80 can communicate with portable terminal 70 via, for example, the Internet and provides portable terminal 70 with an application to use intraoral camera 10. For instance, the user downloads the application from cloud server 80 and installs the application on portable terminal 70. In addition, cloud server 80 obtains a dentition image captured by intraoral camera 10 via portable terminal 70.

The intraoral camera system includes, as main elements that controls the system, central controller 50, image processor 52, LED controller 54, lens driver 56, and position sensor 90. Image processor 52 performs image processing for a dentition image captured by image sensor 14. LED controller 54 controls LEDs 26A to 26D. Lens driver 56 controls actuator 36 that is a composition adjustment mechanism and actuator 40 that is a focus adjustment mechanism.

In addition, the intraoral camera system includes wireless communication module 58 that wirelessly communicates with portable terminal 70 and power supply controller 60 that supplies power to, for example, central controller 50.

Central controller 50 of the intraoral camera system is incorporated into, for example, handle 10b of intraoral camera 10. For instance, central controller 50 includes controller 62, such as a CPU or an MPU, that performs various processing tasks described later and memory 64, such as RAM or ROM, storing programs used to cause controller 62 to perform the various processing tasks. It should be noted that in addition to the programs, dentition images captured by image sensor 14 (image data) and various setting data items are stored in memory 64.

Image processor 52 is incorporated into, for example, handle 10b of intraoral camera 10. On the basis of a control signal from controller 62 of central controller 50, image processor 52 obtains a dentition image captured by image sensor 14 (image data), performs the image processing for the obtained dentition image, and outputs, to central controller 50, the dentition image that has undergone the image processing. Image processor 52 is, for example, a circuit and performs, for the dentition image, the image processing such as noise removal and automatic white balance (AWB) adjustment. Controller 62 transmits the dentition image output by image processor 52 to portable terminal 70 via wireless communication module 58. Portable terminal 70 displays the transmitted dentition image on touch screen 72. In this way, touch screen 72 displays the dentition image to the user.

LED controller 54 is incorporated into, for example, handle 10b of intraoral camera 10 and turns on and off first to fourth LEDs 26A to 26D on the basis of a control signal from controller 62. LED controller 54 is, for example, a circuit. When for instance the user performs an operation to start intraoral camera 10 for touch screen 72 of portable terminal 70, portable terminal 70 transmits a signal corresponding to the operation to controller 62 via wireless communication module 58. On the basis of the received signal, controller 62 transmits the control signal to LED controller 54 to turn on first to fourth LEDs 26A to 26D.

Lens driver 56 is incorporated into, for example, handle 10b of intraoral camera 10 and controls actuator 36, which is the composition adjustment mechanism, and actuator 40, which is the focus adjustment mechanism, on the basis of control signals from controller 62 of central controller 50. Lens driver 56 is, for example, a circuit. When for instance the user performs operations regarding composition adjustment and focus adjustment for touch screen 72 of portable terminal 70, portable terminal 70 transmits signals corresponding to the operations to central controller 50 via wireless communication module 58. On the basis of the received signals, controller 62 of central controller 50 transmits the control signals to lens driver 56 to perform composition adjustment and focus adjustment. In addition, for instance, on the basis of the dentition image received from image processor 52, controller 62 calculates the amount of control for actuator 36 necessary to perform composition adjustment and the amount of control for actuator 40 necessary to perform focus adjustment. Then, control signals corresponding to the calculated amounts of control are transmitted to lens driver 56.

Wireless communication module 58 is incorporated into, for example, handle 10b of intraoral camera 10 and wirelessly communicates with portable terminal 70 on the basis of a control signal from controller 62. Wireless communication module 58 performs, with portable terminal 70, wireless communication that complies with an existing communication standard, such as Wi-Fi (registered trademark) or Bluetooth (registered trademark). Intraoral camera 10 transmits a dentition image showing tooth D to portable terminal 70 via wireless communication module 58, and portable terminal 70 transmits an operation signal to intraoral camera 10 via wireless communication module 58.

In the embodiment, power supply controller 60 is incorporated into handle 10b of intraoral camera 10 and distributes the power of battery 66 to central controller 50, image processor 52, LED controller 54, lens driver 56, and wireless communication module 58. Power supply controller 60 is, for example, a circuit. It should be noted that in the embodiment, battery 66 is a rechargeable battery (secondary battery), and external charger 69 connected to a commercial power supply wirelessly recharges battery 66 via coil 68 included in intraoral camera 10.

Position sensor 90 is used to detect the orientation and position of intraoral camera 10 and is, for example, a multi-axis (here, x, y, and z-axis, that is, three-axis) acceleration sensor. For instance, position sensor 90 may be a six-axis sensor including a three-axis acceleration sensor and a three-axis gyro sensor. For instance, as illustrated in FIG. 1, the z-axis is identical to optical axis LA. The y-axis is parallel to an imaging plane and extends in a longitudinal direction of intraoral camera 10. In addition, the x-axis is parallel to the imaging plane and orthogonal to the y-axis. Output (sensor data) for each axis of position sensor 90 is transmitted to portable terminal 70 via central controller 50 and wireless communication module 58.

A piezo-resistive type, capacitive type, or heat detection type MEMS sensor may be used as position sensor 90. Although not illustrated in the figure, it is preferable to provide a correction circuit for correcting, for example, the balance of sensor sensitivity between the axes, the temperature characteristics of sensitivity, and temperature drift. In addition, a bandpass filter (low pass filter) for removing dynamic acceleration components and a noise may be provided. A noise can be reduced also by smoothing a waveform output by the acceleration sensor.

Figure 3:
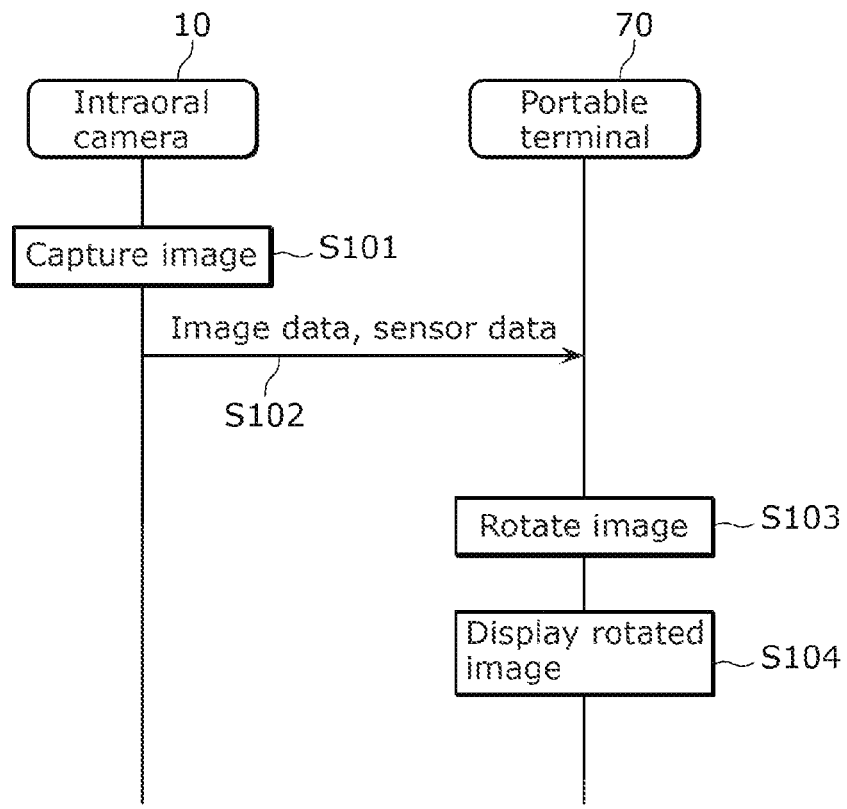
FIG. 3 illustrates a procedure of an intraoral-image capturing operation performed by the intraoral camera system according to the embodiment.

Hereinafter, an intraoral-image capturing operation performed by the intraoral camera system is described. FIG. 3 illustrates a procedure of an intraoral-image capturing operation performed by the intraoral camera system. It should be noted that the processing illustrated in FIG. 3 is, for example, real-time processing and is performed each time image data made up of one or more frames is obtained.

When the user captures an image of teeth and gums inside their mouth by using intraoral camera 10, image data is generated (S101). Intraoral camera 10 transmits, to portable terminal 70, the captured image data and sensor data obtained by position sensor 90 during image capturing (S102). It should be noted that the image data may be a video or one or more still images. In addition, if the image data is a video or includes two or more still images, sensor data is transmitted for each video frame or each still image. It should be noted that if the image data is a video, sensor data may be transmitted every two or more frames.

In addition, the image data and the sensor data may be transmitted in real time or together after a series of image capturing (for example, images of all the teeth inside the user's mouth are captured).

Portable terminal 70 rotates the received image data according to the received sensor data (S103) and displays rotated image data (S104).

By using intraoral camera 10 of such an intraoral camera system, the user can capture an intraoral image showing the interior of their mouth and check their intraoral condition displayed on portable terminal 70. Thus, the user can readily check the health condition of their teeth, for instance.

For instance, portable terminal 70 may create a three-dimensional model of two or more teeth inside the user's mouth from two or more captured image data items. In addition, portable terminal 70 may display an image based on the created three-dimensional model.

It should be noted that in an example described here, portable terminal 70 rotates a tooth image. However, intraoral camera 10 may perform a part or all of the rotation processing.

Figure 4:
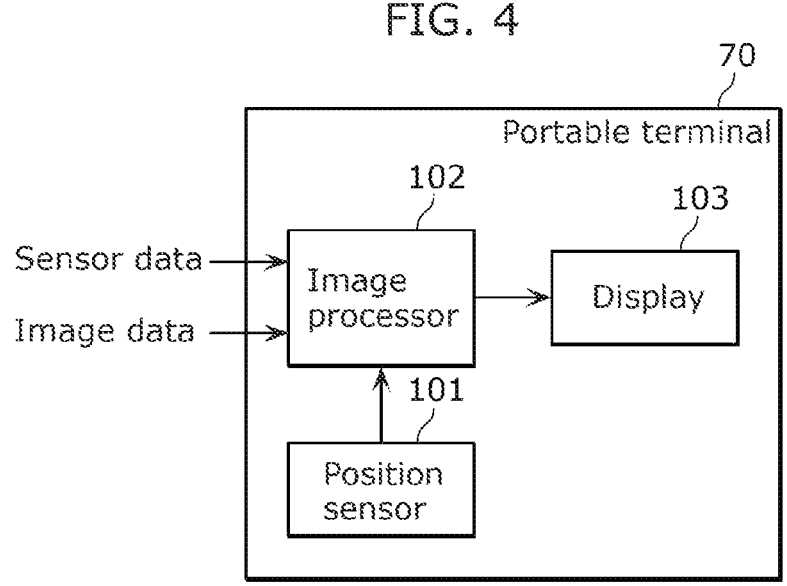
FIG. 4 is a functional block of a portable terminal according to the embodiment.

FIG. 4 is a functional block diagram of portable terminal 70. Portable terminal 70 includes position sensor 101, image processor 102, and display 103.

Position sensor 101 is used to detect the orientation and position of portable terminal 70 and is, for example, a multi-axis (e.g., three-axis) acceleration sensor.

According to sensor data transmitted from intraoral camera 10 and sensor data obtained by position sensor 101, image processor 102 performs image processing including image data rotation processing. The function of image processor 102 is achieved by a program executer, such as a CPU or a processor, reading and executing a software program stored in a recording medium, such as a hard disk or semiconductor memory.

Display 103 is the display device of portable terminal 70 and displays image data that has undergone the image processing by image processor 102.

Figure 5:
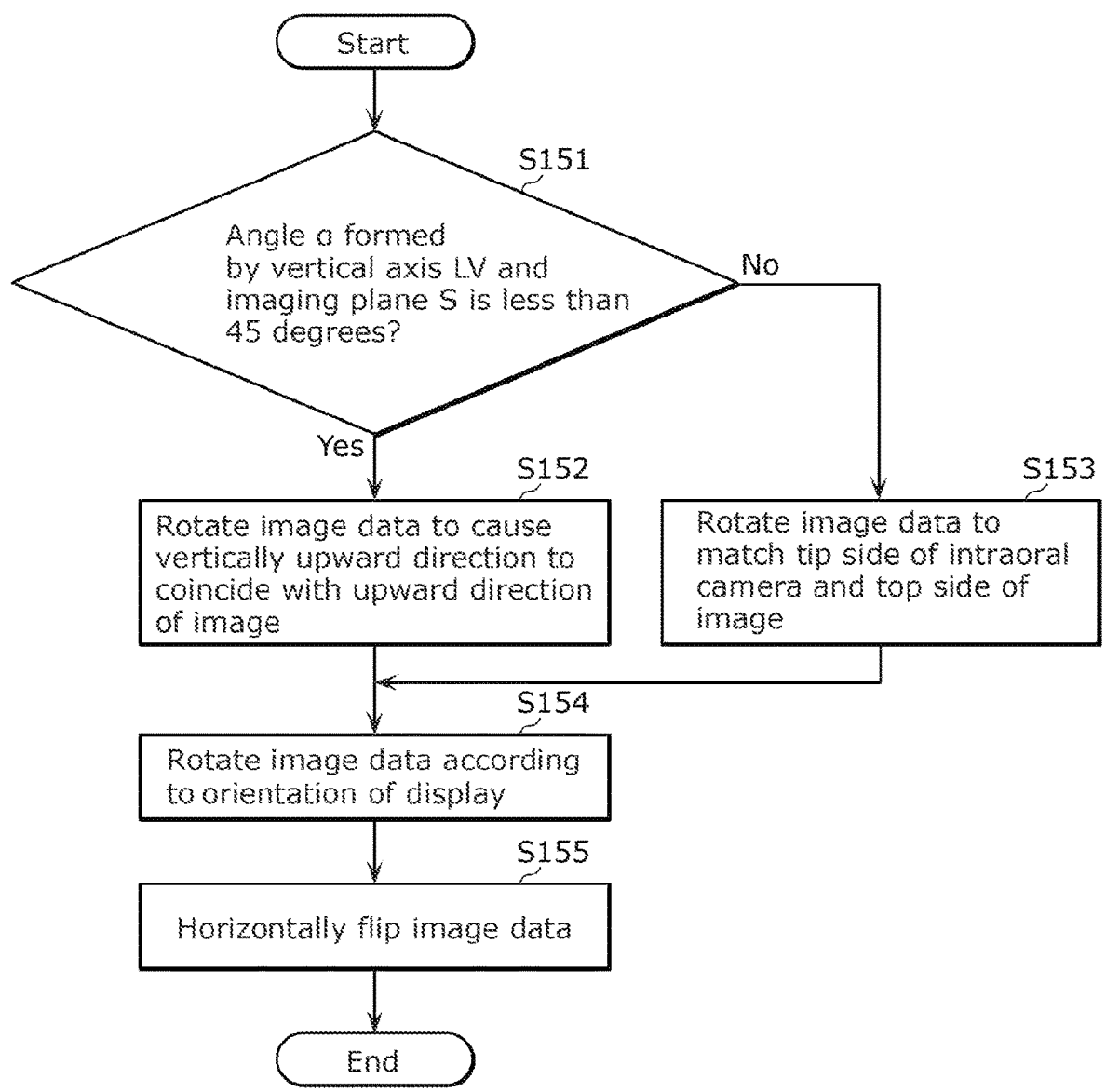
FIG. 5 is a flowchart illustrating image processing according to the embodiment.

FIG. 5 is a flowchart illustrating the image processing performed by image processor 102. Image processor 102 determines whether angle α formed by vertical axis LV in real space and imaging plane S is 0 degrees or greater and less than 45 degrees (S151). Here, the orientation of imaging plane S is calculated from the sensor data obtained by intraoral camera 10.

Figure 6:
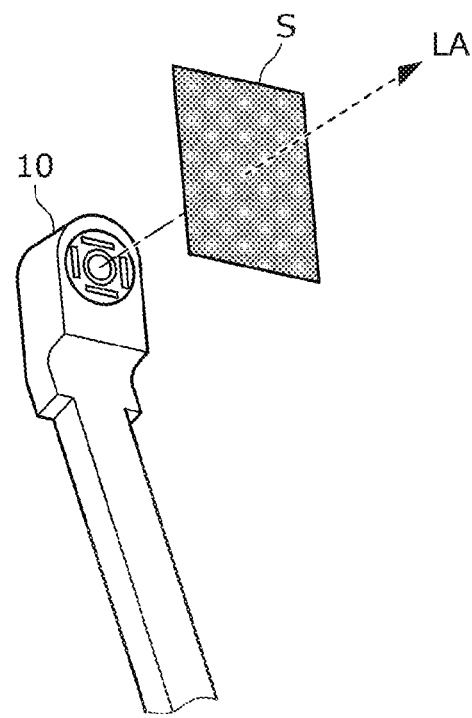
FIG. 6 schematically illustrates a relationship between the intraoral camera according to the embodiment and an imaging plane.

FIG. 6 schematically illustrates a relationship between intraoral camera 10 and imaging plane S. Imaging plane S is perpendicular to optical axis LA.

Figure 7:
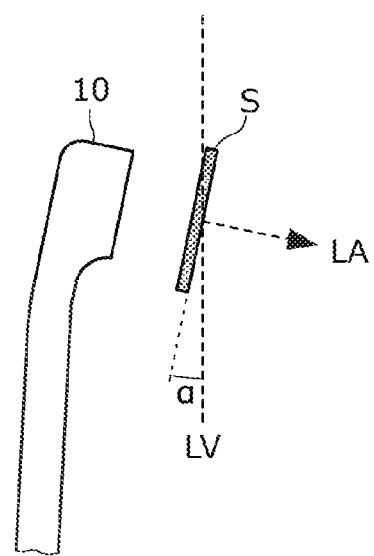
FIG. 7 illustrates an example of angle $\alpha$ formed by a vertical axis and the imaging plane according the embodiment.
Figure 8:
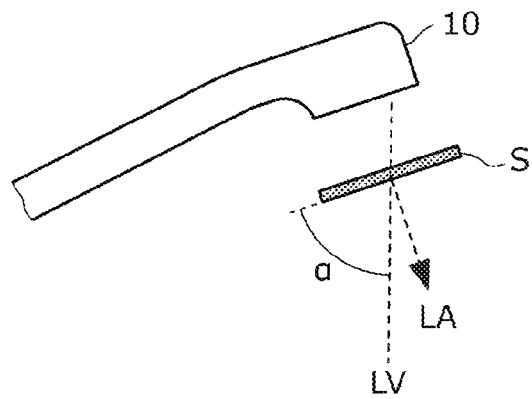
FIG. 8 illustrates an example of angle $\alpha$ formed by the vertical axis and the imaging plane according the embodiment.

FIGS. 7 and 8 each illustrate an example of angle α formed by vertical axis LV and imaging plane S. Here, angle α ranges from 0 degrees to 90 degrees. In addition, angle α is also referred to as 90 degrees minus (an angle formed by vertical axis LV and optical axis LA).

In the example in FIG. 7, angle α is less than 45 degrees, and imaging plane S has a near-vertical angle. In the example in FIG. 8, angle α is 45 degrees or greater, and imaging plane S has a near-horizontal angle. Here, when an image of the side surfaces of teeth (the buccal or lingual surfaces of the teeth) is captured, as illustrated in FIG. 7, imaging plane S has a near-vertical angle. When an image of the tops of teeth (the occlusal surfaces of the teeth) is captured, imaging plane S has a near-horizontal angle. Thus, if angle α is less than 45 degrees (Yes in S151), image processor 102 determines that an image of the side surfaces of teeth is being captured. If angle α is 45 degrees or greater (No in S151), image processor 102 determines that an image of the tops of teeth is being captured.

It should be noted that in the example described here, a threshold for determining the direction in which a tooth image is captured is set to 45 degrees. However, the threshold is not limited to 45 degrees. For instance, the threshold may fall within the range from 40 degrees to 50 degrees or the range from 30 degrees to 60 degrees.

First, the case in which angle α is less than 45 degrees (Yes in S151) is described. If angle α is less than 45 degrees (Yes in S151), image processor 102 determines that the user is capturing a tooth image from the buccal or lingual side. Image processor 102 rotates image data to cause the vertically upward direction to coincide with the upward direction (direction from bottom to top) of the image (S152). Hereinafter, a specific example of the processing is described.

Figure 9:
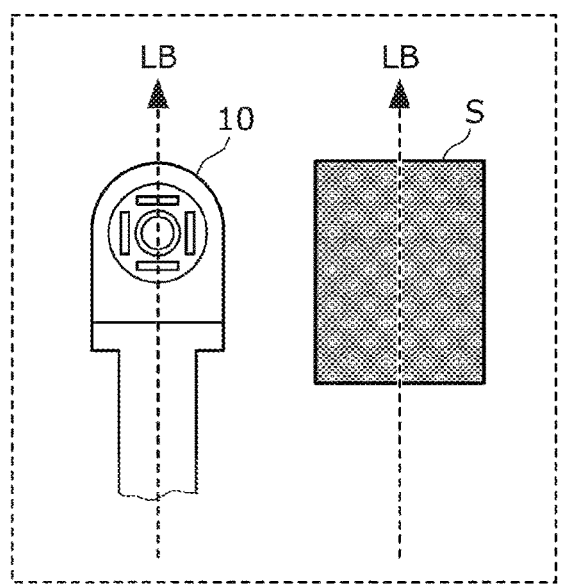
FIG. 9 illustrates an example of axial direction LB of the intraoral camera according to the embodiment.

FIG. 9 illustrates an example of axial direction LB of intraoral camera 10. Direction LB passes through the center of intraoral camera 10 in a longitudinal direction of intraoral camera 10 and is the direction from handle 10b toward head 10a. In addition, in the example, direction LB passes through the center of imaging plane S in a vertical direction (column direction) of imaging plane S (image data). In other words, the top side of the image data generated by intraoral camera 10 corresponds to the tip side of intraoral camera 10 (head 10a side), and the bottom side of the image data corresponds to the root side of intraoral camera 10 (handle 10b side). In addition, direction LB is calculated from sensor data obtained by intraoral camera 10.

Figure 10:
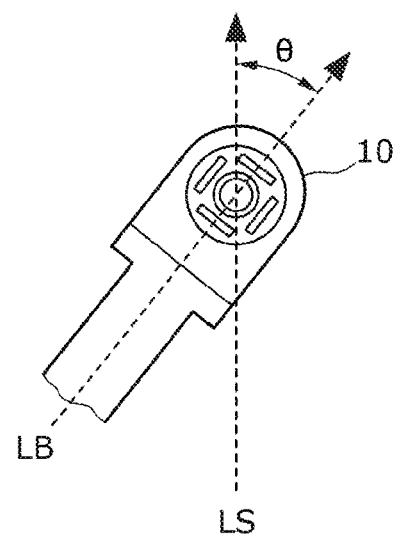
FIG. 10 illustrates examples of direction LB and direction LS according to the embodiment.
Figure 11:
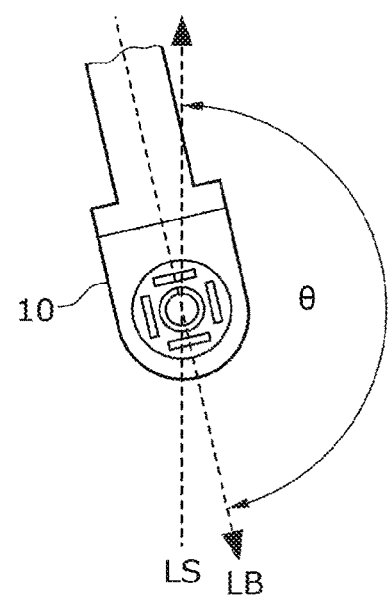
FIG. 11 illustrates examples of direction LB and direction LS according to the embodiment.

FIGS. 10 and 11 each illustrate examples of direction LB and direction LS. Direction LS is the vertically upward direction along the vertical axis. In addition, angle θ in each of FIGS. 10 and 11 is an angle formed by direction LB and direction LS and ranges from 0 degrees to 180 degrees. Image processor 102 rotates the image data by angle θ to cause the vertically upward direction to coincide with the upward direction of the image. As illustrated in FIG. 9, if the top side of the image data already corresponds to the tip side of intraoral camera 10, image processor 102 does not rotate the image data.

An operation performed by image processor 102 when the user is capturing an image of maxillary anterior teeth (central incisor(s), lateral incisor(s)) is described as an example.

Figure 12A:
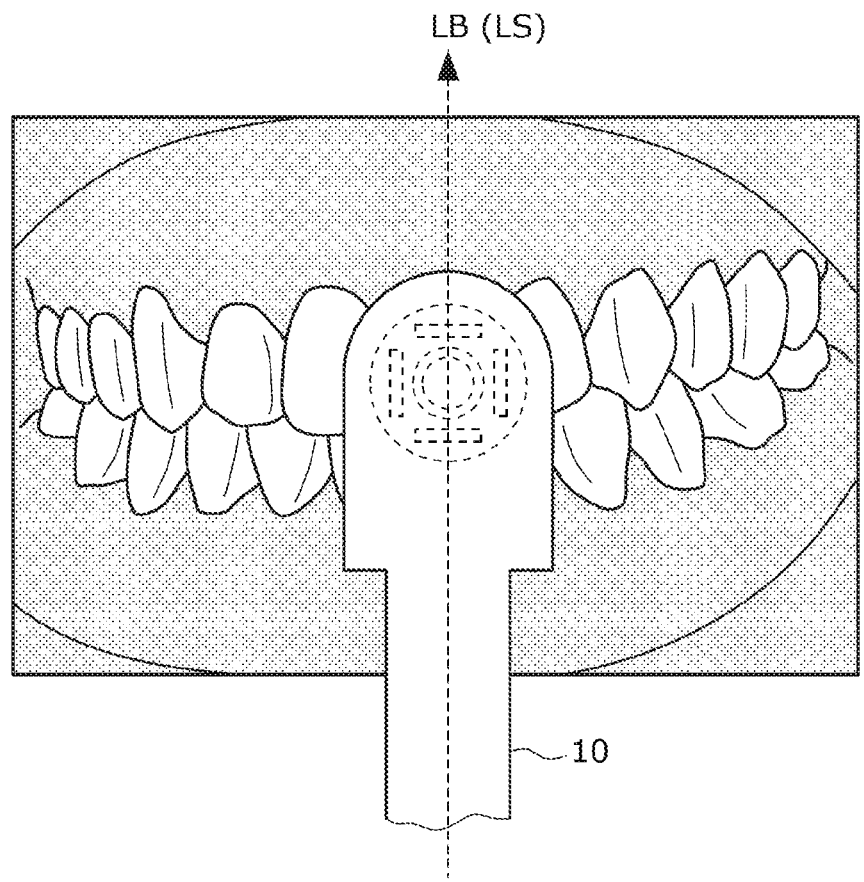
FIG. 12A illustrates an example of an image capturing state according to the embodiment.

FIG. 12A illustrates a state in which the user who is vertically holding intraoral camera 10 is capturing an image of maxillary anterior teeth from the buccal side (labial side). In FIG. 12A, direction LB is parallel to direction LS.

Figure 12B:
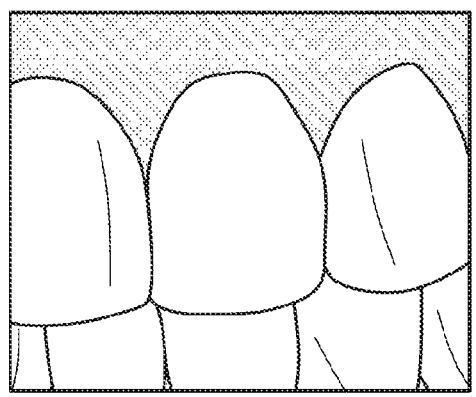
FIG. 12B illustrates an example of a captured image according to the embodiment.

FIG. 12B illustrates an example of the image of the anterior teeth captured in the state illustrated in FIG. 12A. The image data is displayed so that the tip side (head 10a side) of intraoral camera 10 matches the top side of the image. Since direction LB is parallel to direction LS, as known from FIG. 12B, a gum area (also referred to as a gingival area) including gums (also referred to as gingivae) is displayed above a tooth area. Thus, the user can intuitively understand their tooth condition.

Figure 13A:
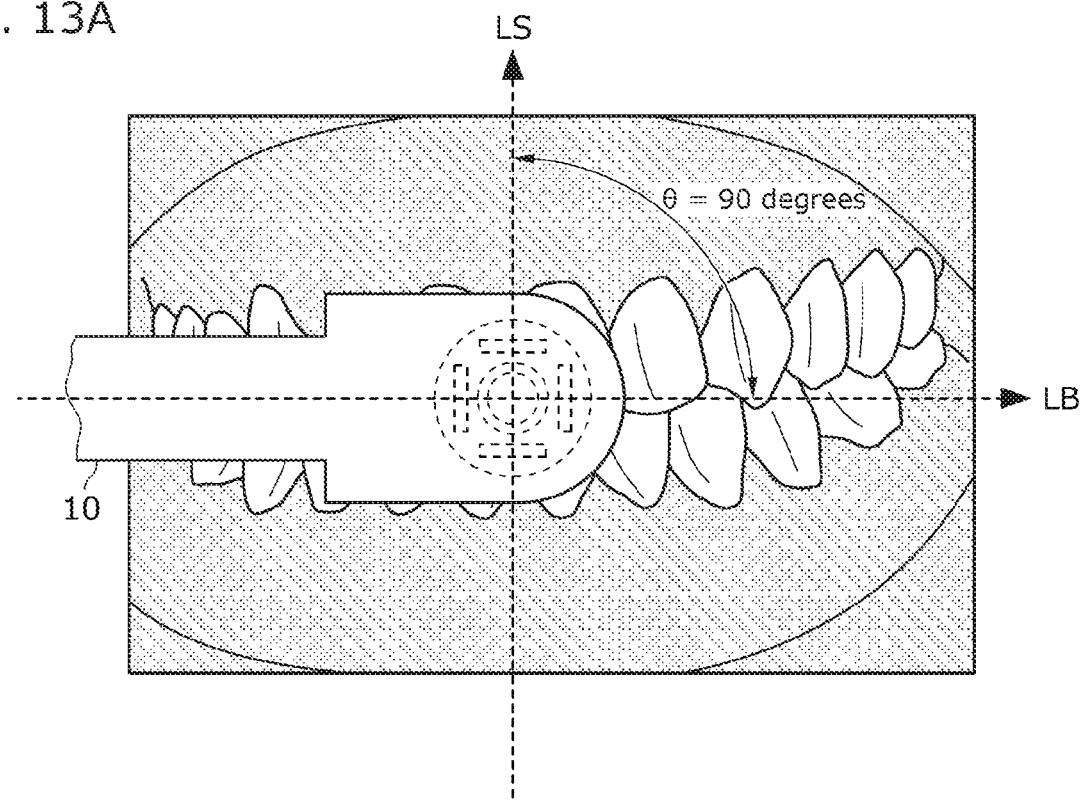
FIG. 13A illustrates an example of an image capturing state according to the embodiment.

Meanwhile, FIG. 13A illustrates a state in which the user who is horizontally holding intraoral camera 10 is capturing an image of maxillary anterior teeth from the buccal side (labial side). In FIG. 13A, angle θ formed by direction LB and direction LS is 90 degrees.

Figure 13B:
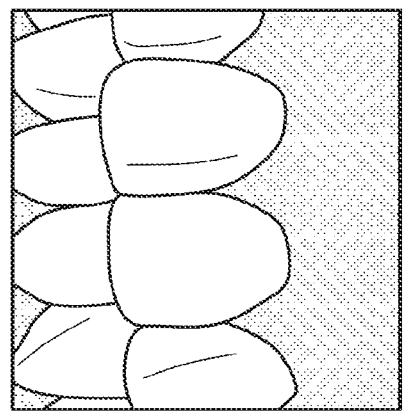
FIG. 13B illustrates an example of a captured image according to the embodiment.

FIG. 13B illustrates an example of the image of the anterior teeth captured in the state illustrated in FIG. 13A. The image data is displayed so that the top side of the image matches the tip side (head 10a side) of intraoral camera 10. Thus, the gum area is displayed on the right side, and the tooth area is displayed on the left side.

Figure 13C:
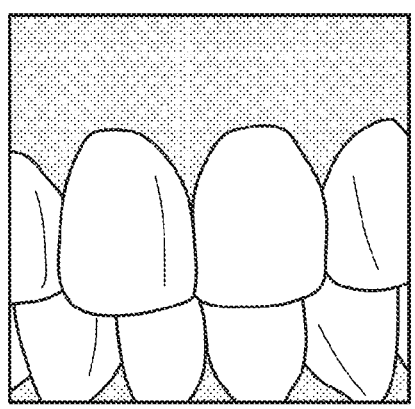
FIG. 13C illustrates an example of the image that has undergone the image processing according to the embodiment.

FIG. 13C illustrates the image of the anterior teeth that has undergone the processing by image processor 102. Image processor 102 rotates the image data by an angle of 90 degrees to cause the vertically upward direction to coincide with the upward direction of the image and displays the rotated image data. Thus, in the displayed image, the gum area including the gums is above the tooth area, which enables the user to intuitively understand their tooth condition.

Figure 14:
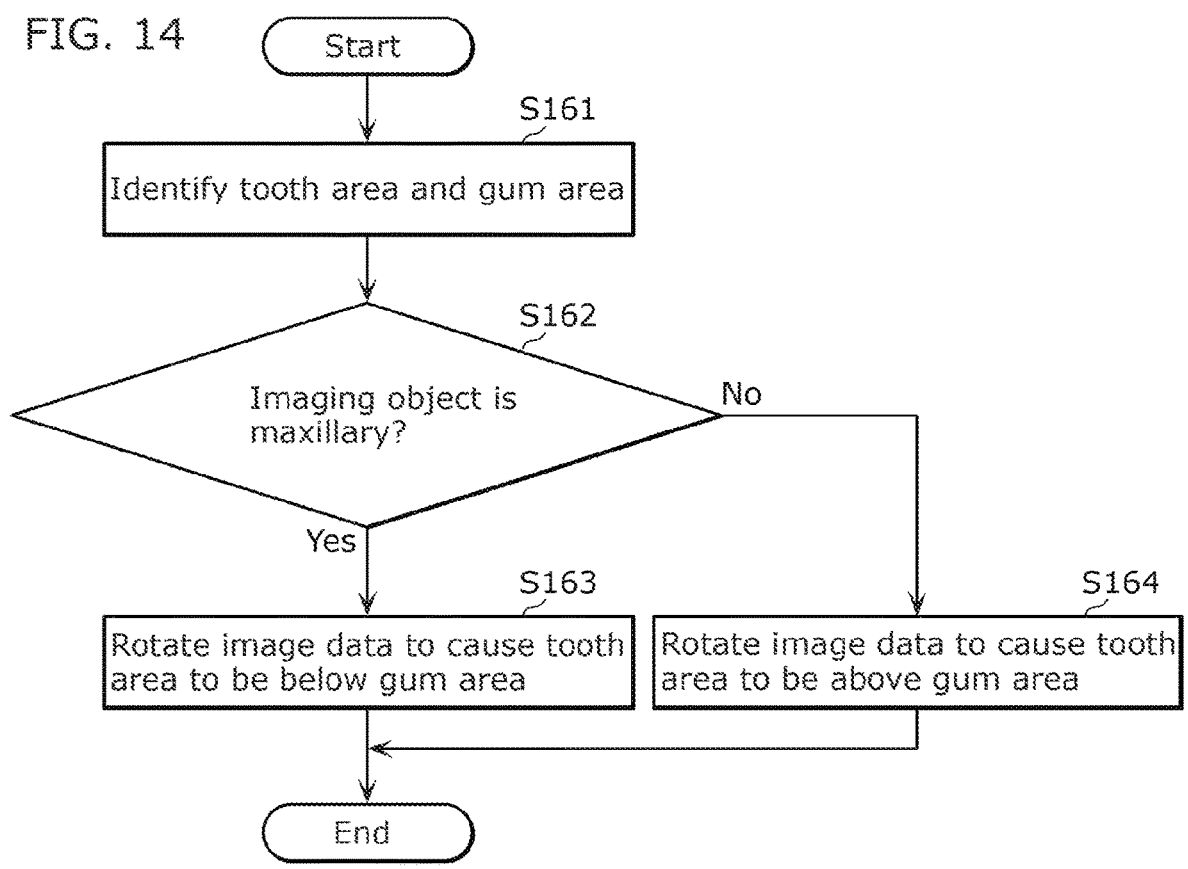
FIG. 14 is a flowchart illustrating another specific example of rotation processing according to the embodiment.

It should be noted that the following method may be used as a specific example of the rotation processing. FIG. 14 is a flowchart illustrating another specific example of the rotation processing. Image processor 102 identifies a tooth area including teeth and a gum area including gums from image data (S161). For instance, image processor 102 identifies the tooth area and the gum area from the image data by performing, for example, image analysis using the amounts of characteristics.

Image processor 102 determines whether the current imaging object is maxillary or mandibular (S162). For instance, intraoral camera 10 receives interference from the lips or cheeks while being operated along a row of teeth inside the mouth. Thus, when a maxillary-dentition image is captured, imaging plane S faces upward to no small extent. When a mandibular-dentition image is captured, imaging plane S faces downward to no small extent. Thus, if the orientation of imaging plane S (the direction of optical axis LA) is tilted upward relative to the horizontal, image processor 102 determines that the imaging object is maxillary. If the orientation of imaging plane S (the direction of optical axis LA) is tilted downward relative to the horizontal, image processor 102 determines that the imaging object is mandibular.

Rather than image processor 102 determining whether the imaging object is maxillary or mandibular according to the orientation of imaging plane S (the direction of optical axis LA), the user may for instance input whether the imaging object is maxillary or mandibular into portable terminal 70. The portion to be the imaging object input into portable terminal 70 by the user is input into image processor 102.

If the imaging object is maxillary (Yes in S162), image processor 102 rotates the image data to cause the tooth area to be below the gum area (S163). Meanwhile, if the imaging object is mandibular (No in S162), image processor 102 rotates the image data to cause the tooth area to be above the gum area (S164). Thus, image processor 102 can rotate the image data to cause the vertically upward direction to coincide with the upward direction of the image.

It should be noted that rotating the image data to cause the vertically upward direction to coincide with the upward direction of the image, in step S152 is not limited to rotation of the image data that leads to perfect correspondence between the vertically upward direction and the upward direction of the image and may allow a predetermined deviation from perfect correspondence. In addition, the processing may include rotation of the image data that causes the vertically upward direction to come closer to the upward direction of the image in comparison with the image data before rotation.

Thus, if an image of the side surfaces of teeth is captured, image processor 102 rotates the image data to cause the vertically upward direction to coincide with the upward direction of the image. This enables the user to check, on portable terminal 70, the image reflecting the real vertical positional relationship. Thus, the user can intuitively understand their tooth condition, which can improve user convenience.

Descriptions are provided with reference to FIG. 5 again. Next, the case in which angle α is 45 degrees or greater (No in S151) is described below. If angle α is 45 degrees or greater (No in S151), image processor 102 determines that the user is capturing an image of the tops of teeth. Image processor 102 rotates the image data so as to match the tip side of intraoral camera 10 and the top side of the image (S153).

Here, if the image of the tops of the teeth is being captured, a tilt relative to the vertical direction has a low impact. Thus, rotation based on the tilt relative to the vertical direction, as performed in step S152 is not performed. Meanwhile, by displaying the image data in which the tip side of intraoral camera 10 matches the top side of the image, it is possible to display the image in such a way that the tops of the teeth are viewed from outside the mouth. Thus, the user can intuitively understand their tooth condition, which can improve user convenience.

It should be noted that rotating the image data so as to match the tip side of intraoral camera 10 and the top side of the image, in step S153 is not limited to rotation of the image data that leads to perfect matching between the tip side of intraoral camera 10 and the top side of the image and may allow a predetermined deviation from perfect alignment.

After step S152 or S153, image processor 102 rotates the image data according to the orientation of display 103 (the orientation of portable terminal 70) (S154). Specifically, regardless of the orientation of display 103 (portable terminal 70), image processor 102 rotates the image data to cause the top side of the displayed image to be at a higher position in real space.

Figure 15:
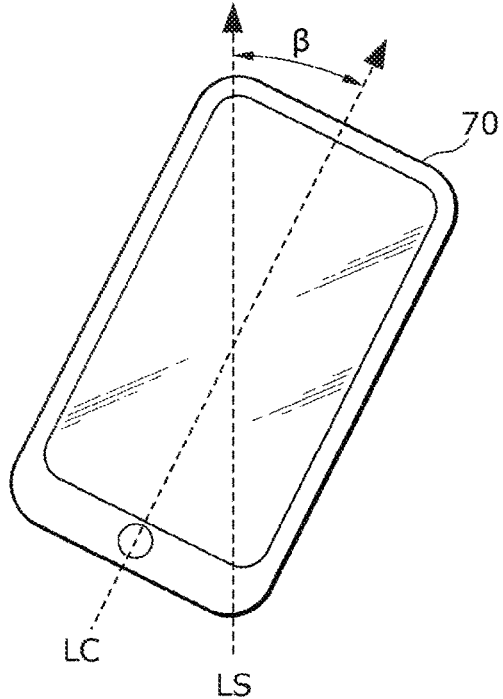
FIG. 15 illustrates a tilt of a portable terminal according to the embodiment.

FIG. 15 illustrates a tilt of portable terminal 70. As illustrated in FIG. 15, if portable terminal 70 is tilted at angle β relative to vertically upward direction LS, image processor 102 rotates the image data by angle β. It should be noted that direction LC in FIG. 15 is a longitudinal direction of portable terminal 70 and the direction from the bottom of portable terminal 70 toward the top during normal use. For instance, angle β is an angle formed by direction LS and direction LC.

Thus, for instance, in a case in which the user captures an image of their teeth by intraoral camera 10 held by one hand while holding portable terminal 70 with the other hand, even if portable terminal 70 is tilted, the user can check, on portable terminal 70, the image reflecting the real vertical positional relationship. Thus, the user can intuitively understand their tooth condition, which can improve user convenience.

Image processor 102 horizontally flips the image data (S155). This enables the user to check their teeth in the same state as their teeth are reflected on a mirror. Thus, the user can intuitively understand their tooth condition, which can improve user convenience.

It should be noted that in the example of the above descriptions, the orientation of intraoral camera 10, the orientation of portable terminal 70, and the imaging direction are identified using the three-axis acceleration sensor of position sensor 90 and the three-axis acceleration sensor of position sensor 101. However, the orientation of intraoral camera 10, the orientation of portable terminal 70, and the imaging direction may be identified using three-axis gyro sensors. The three-axis gyro sensors output, for example, the amount of angle change because of movement around the x-axis, the amount of angle change because of movement around the y-axis, and the amount of angle change because of movement around the z-axis. That is, for the three-axis gyro sensors, in a state in which initial states for the x-axis, the y-axis, and the z-axis are optionally set, the amount of change for each axis is added. Then, the orientation of intraoral camera 10, the orientation of portable terminal 70, and the imaging direction are identified.

It should be noted that the orientation of intraoral camera 10, the orientation of portable terminal 70, and the imaging direction may be identified using both a three-axis acceleration sensor and a three-axis gyro sensor.

As described above, the intraoral camera system includes an imaging unit (e.g., intraoral camera 10), position sensor 90, image processor 102, and display 103. The imaging unit (e.g., intraoral camera 10) generates image data when an image of teeth inside the user's mouth is captured manually. Position sensor 90 detects the orientation of the imaging unit (e.g., intraoral camera 10). Image processor 102 rotates the image data according to the orientation of the imaging unit (e.g., intraoral camera 10) detected by position sensor 90. Display 103 displays the rotated image data. In this manner, the intraoral camera system can properly display the captured image of the teeth.

For instance, according to the orientation of the imaging unit (e.g., intraoral camera 10), image processor 102 rotates the image data to cause the vertically upward direction in real space to coincide with the upward direction of the image. Thus, for instance, the user can check the image reflecting the real vertical positional relationship. Accordingly, the user can intuitively understand their tooth condition.

For instance, if first angle α formed by imaging plane S of the imaging unit (e.g., intraoral camera 10) and vertical axis LV is less than a predetermined second angle (e.g., 45 degrees), image processor 102 rotates the image data according to the orientation of the imaging unit (e.g., intraoral camera 10) to cause the vertically upward direction in real space to coincide with the upward direction of the image.

For instance, the imaging unit (e.g., intraoral camera 10) includes handle 10b, head 10a, and neck 10c. Handle 10b is designed to be held by the user. Head 10a includes an image sensor that generates image data. Neck 10c connects handle 10b to head 10a. If first angle α is the second angle or greater, image processor 102 rotates the image data so as to match head 10a side of the imaging unit (e.g., intraoral camera 10) and the top side of the image.

For instance, the imaging unit (e.g., intraoral camera 10) includes handle 10b, head 10a, and neck 10c. Handle 10b is designed to be held by the user. Head 10a includes an image sensor that generates image data. Neck 10c connects handle 10b to head 10a. Image processor 102 rotates the image data by third angle θ formed by first direction LB from handle 10b toward head 10a and second direction LV that is the vertically upward direction.

For instance, as illustrated in FIG. 14, according to the orientation of the imaging unit (e.g., intraoral camera 10), image processor 102 determines whether the image data includes a maxillary image or a mandibular image (S162). If the image data includes a maxillary image, image processor 102 rotates the image data to cause the tooth area to be below the gum area in the image data (S163). If the image data includes a mandibular image, image processor 102 rotates the image data to cause the tooth area to be above the gum area in the image data (S164).

For instance, image processor 102 further horizontally flips the image data (S155), and display 103 displays the rotated and horizontally flipped image data. Thus, for instance, the user can check their teeth in the same state as their teeth are reflected on a mirror. Accordingly, the user can intuitively understand their tooth condition.

For instance, image processor 102 further rotates the image data according to the orientation of display 103 (S154). Thus, for instance, the user can check the image reflecting the real vertical positional relationship. Accordingly, the user can intuitively understand their tooth condition.

Hereinafter, variations of the above embodiment are described.

Variation 1

Figure 16:
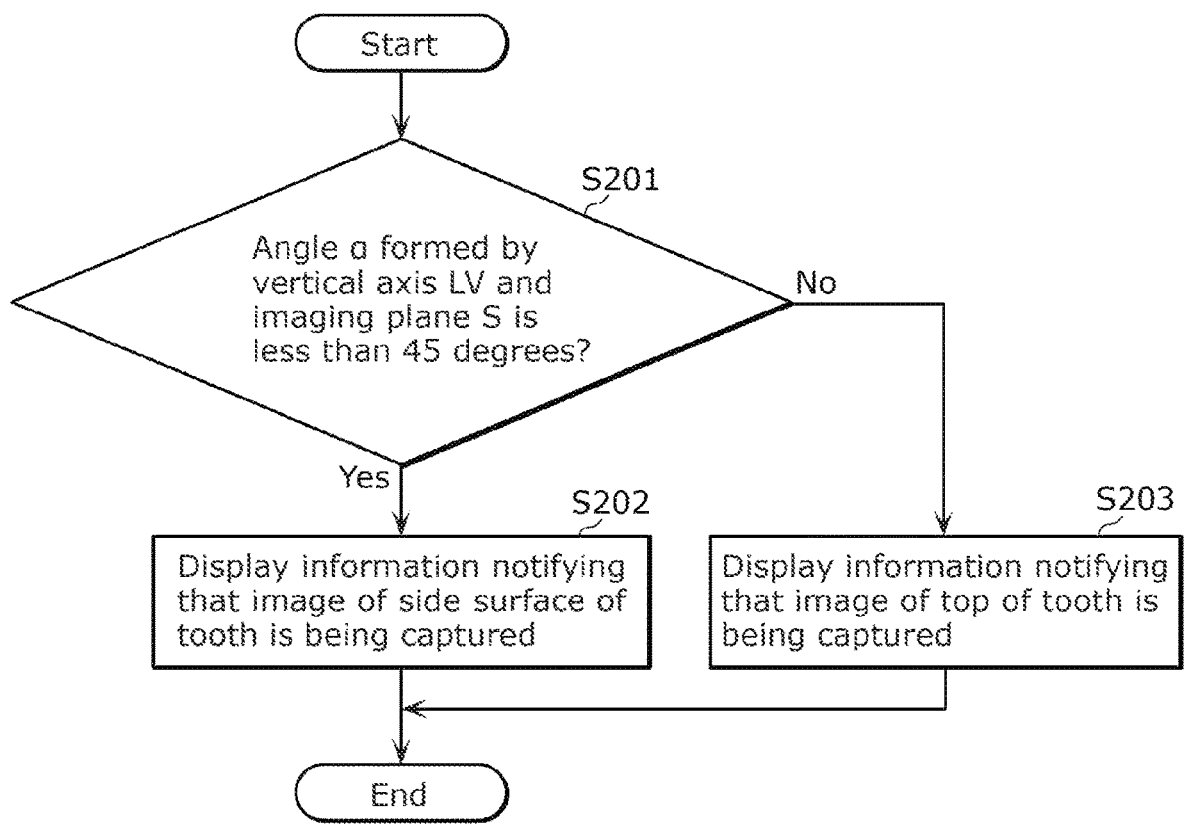
FIG. 16 is a flowchart illustrating image processing according to Variation 1 of the embodiment.

Display 103 may display the result of the above-mentioned determination of the direction in which a tooth image is captured, which is based on the orientation of intraoral camera 10. FIG. 16 is a flowchart illustrating image processing performed by image processor 102 in this case. It should be noted that image processor 102 may perform only the processing illustrated in FIG. 16 or may perform the processing illustrated in FIG. 16 in addition to the above-mentioned processing (for example, the processing illustrated in FIG. 5).

Image processor 102 determines whether angle α formed by vertical axis LV in real space and imaging plane S is 0 degrees or greater and less than 45 degrees (S201). Here, the orientation of imaging plane S is calculated from sensor data obtained by intraoral camera 10. It should be noted that the details of the step is similar to those of S151 in FIG. 5.

Figure 17:
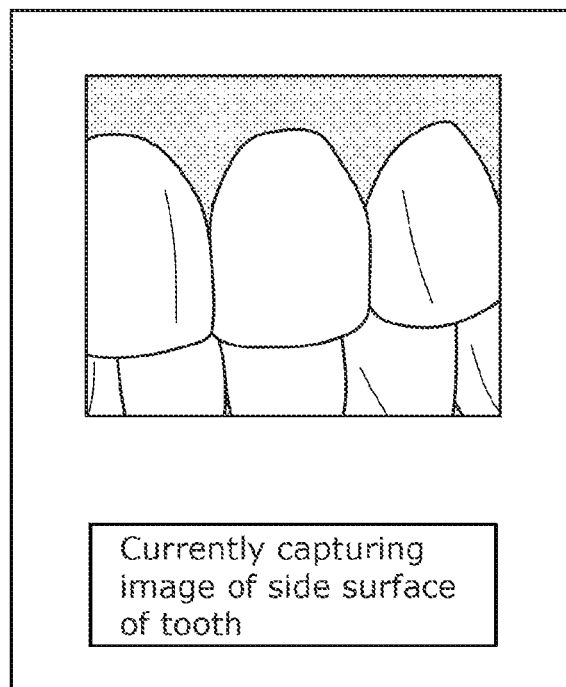
FIG. 17 illustrates a display example according to Variation 1 of the embodiment.

If angle α is less than 45 degrees (Yes in S201), image processor 102 determines that an image of the side surfaces of teeth (the buccal or lingual surfaces of the teeth) is being captured and displays, on display 103, information notifying that the image being captured (displayed) is the image of the side surfaces of the teeth captured inside a user's mouth (S202). FIG. 17 illustrates a display example in this case. As illustrated in FIG. 17, for example, display 103 displays the image being captured and the information notifying that the image of the side surfaces of the teeth is being captured.

Figure 18:
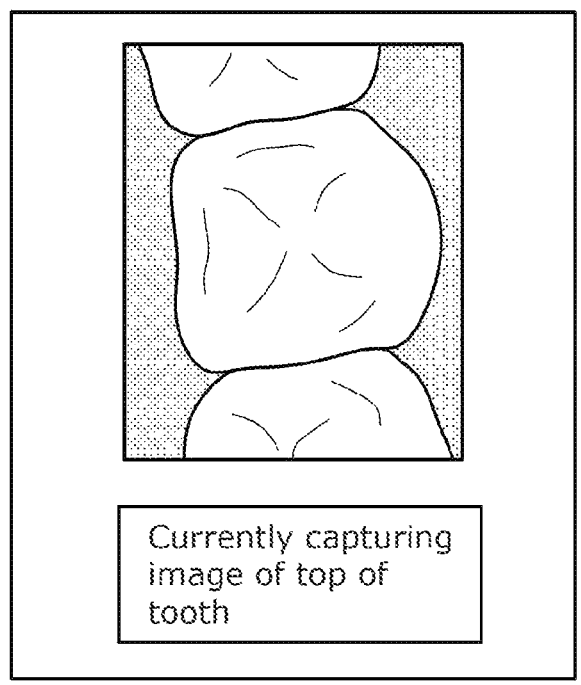
FIG. 18 illustrates a display example according to Variation 1 of the embodiment.

Meanwhile, if angle α is 45 degrees or greater (No in S201), image processor 102 determines that an image of the tops of teeth is being captured and displays, on display 103, information notifying that the image being captured (displayed) is the image of the tops of the teeth captured inside the user's mouth (S203). FIG. 18 illustrates a display example in this case. As illustrated in FIG. 18, for example, display 103 displays the image being captured and the information notifying that the image of the tops of the teeth is being captured.

It should be noted that in the above examples, the direction in which the tooth image is captured is displayed by text (a message). However, text, an illustration, an icon, a sign, and others may be used or a combination of the text, illustration, icon, sign, and others may be used.

In this manner, by displaying the direction in which a tooth image is captured, the user can readily identify the direction in which the tooth image is currently being captured, which can improve user convenience.

Variation 2

In the above examples, for example, the direction in which a tooth image is captured is determined according to whether angle α is less than the predetermined angle (e.g., 45 degrees). However, if angle α is close to the predetermined angle, determination accuracy may decrease. When for instance an image of molars at the back of the mouth is captured, angle α may be close to 45 degrees. Thus, if angle α is close to the predetermined angle, image processor 102 may further perform another determination processing task.

Figure 19:
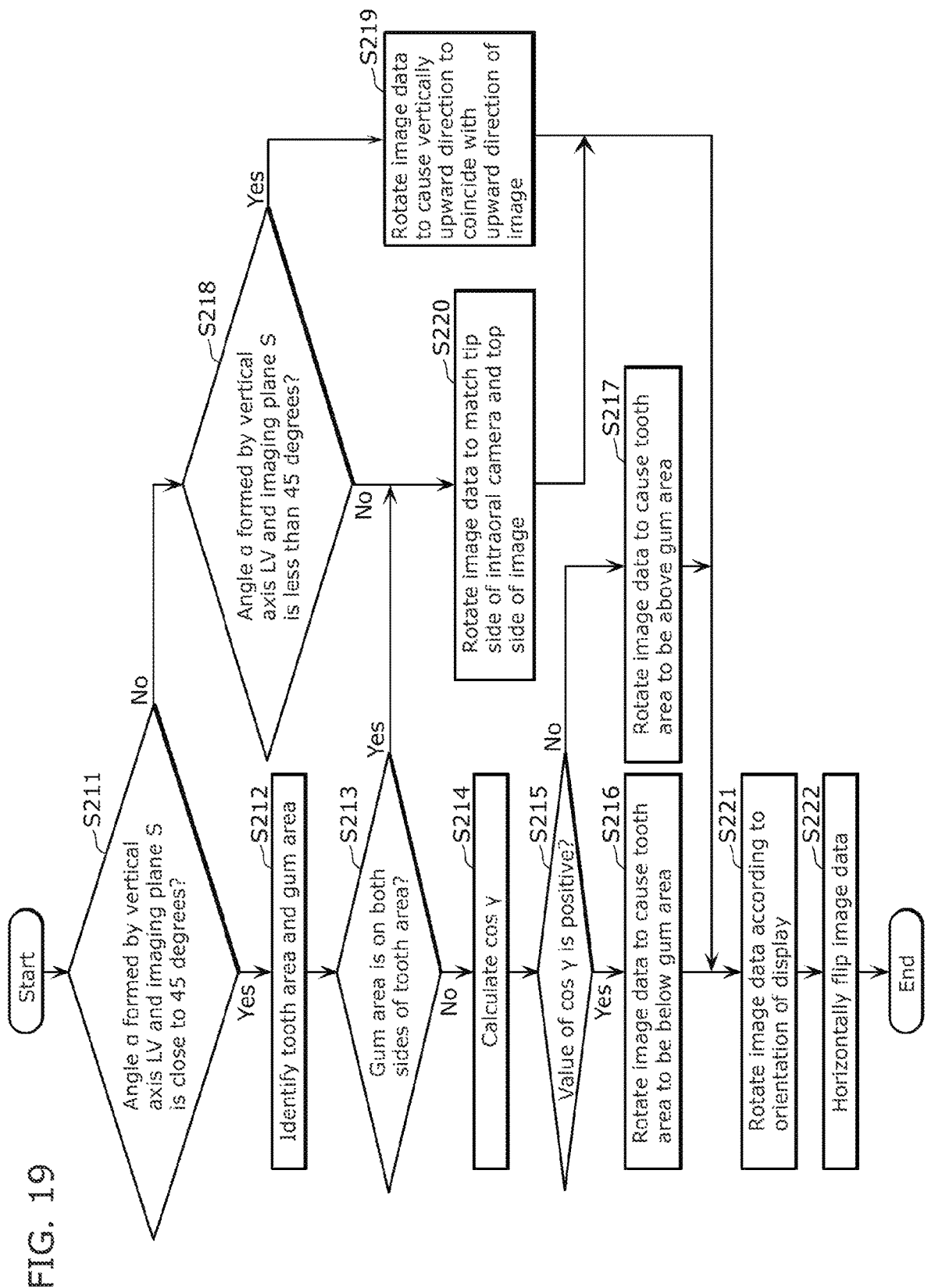
FIG. 19 is a flowchart illustrating image processing according to Variation 2 of the embodiment.

FIG. 19 is a flowchart illustrating image processing performed by image processor 102 in this case. Image processor 102 determines whether angle α formed by vertical axis LV in real space and imaging plane S is close to 45 degrees (S211). It should be noted that an angle range close to 45 degrees may be from 40 degrees to 50 degrees or may be a narrower or broader range. In other words, if a difference between angle α and 45 degrees is less than a predetermined value, image processor 102 determines that angle α is close to 45 degrees.

If angle α is not close to 45 degrees (No in S211), image processor 102 performs processing similar to the processing illustrated in FIG. 5 (S218 to S222). That is, image processor 102 determines whether angle α is 0 degrees or greater and less than 45 degrees (S218).

If angle α is less than 45 degrees (Yes in S218), image processor 102 determines that a user is capturing a tooth image from the buccal or lingual side and rotates image data to cause the vertically upward direction to coincide with the upward direction of the image (S219). Meanwhile, if angle α is 45 degrees or greater (No in S218), image processor 102 determines that the user is capturing an image of the tops of teeth and rotates image data so as to match the tip side of intraoral camera 10 and the top side of the image (S220).

Then, image processor 102 rotates the image data according to the orientation of display 103 (the orientation of portable terminal 70) (S221). Specifically, regardless of the orientation of display 103 (portable terminal 70), image processor 102 rotates the image data to cause the top side of the displayed image to be at a higher position in real space. Image processor 102 horizontally flips the image data (S222). Thus, the user can check their teeth in the same state as their teeth are reflected on a mirror.

Meanwhile, if angle α is close to 45 degrees (Yes in S211), image processor 102 identifies a tooth area including teeth and a gum area including gums from the image data (S212). For instance, image processor 102 identifies the tooth area and the gum area from the image data by performing, for example, image analysis using the amounts of characteristics.

Image processor 102 determines whether the gum area is on both sides of the tooth area or only on one side of the tooth area (S213). If the gum area is on both sides of the tooth area (Yes in S213), image processor 102 determines that the user is capturing an image of the tops of the teeth and rotates the image data so as to match the tip side of intraoral camera 10 and the top side of the image (S220).

Figure 20:
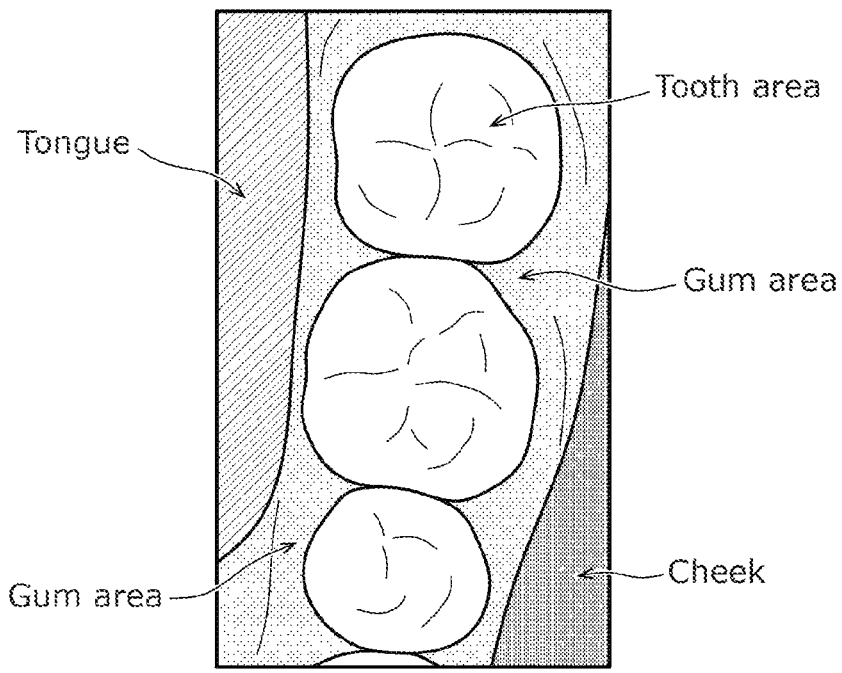
FIG. 20 illustrates an example of a captured image according to Variation 2 of the embodiment.

FIG. 20 illustrates an example of an image of the tops of teeth. As illustrated in FIG. 20, in an image of the tops of teeth, the gum area is on both sides of the tooth area (a row of teeth).

Figure 21:
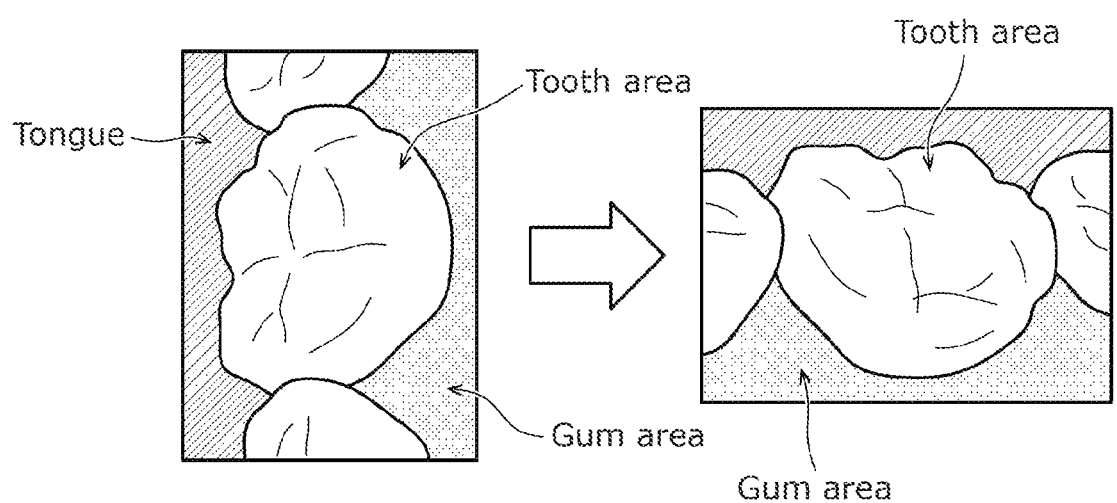
FIG. 21 illustrates an example of a captured image according to Variation 2 of the embodiment.

Meanwhile, if the gum area is only on one side of the tooth area (No in S213), image processor 102 determines that the user is capturing a tooth image from the buccal or lingual side. FIG. 21 illustrates an example of an image of mandibular teeth captured from the buccal side. As illustrated in FIG. 21, in an image captured from the buccal side, the gum area is only on one side of the tooth area (a row of teeth).

Figure 22:
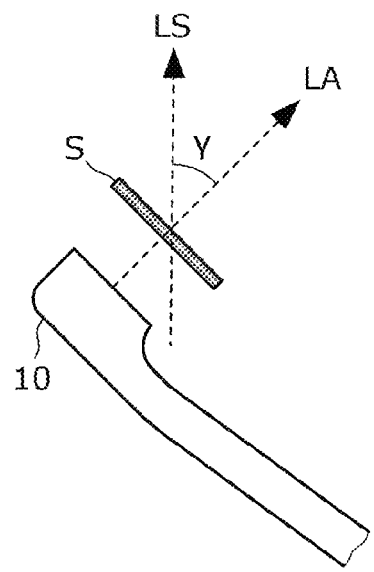
FIG. 22 illustrates an example of angle $\gamma$ according to Variation 2 of the embodiment.
Figure 23:
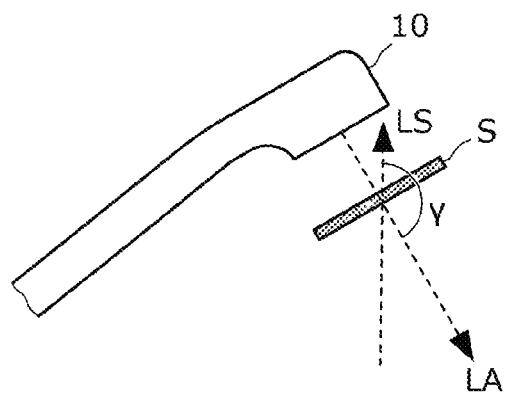
FIG. 23 illustrates an example of angle $\gamma$ according to Variation 2 of the embodiment.

Then, image processor 102 calculates cos γ (S214). FIGS. 22 and 23 each illustrate an example of angle γ. Angle γ is an angle formed by optical axis LA and vertically upward direction LS and ranges from 0 degrees to 180 degrees. Image processor 102 determines whether the value of cos γ is positive or negative (S215). Here, image processor 102 determines whether the value of cos γ is positive or negative. However, the processing is equivalent to determination of whether the inner product of a first vector and a second vector is positive or negative. The first vector has a given value in the direction from image sensor 14 toward a subject along optical axis LA. The second vector has a given value in vertically upward direction LS.

If the value of cos γ is positive (Yes in S215), that is, if angle γ ranges from 0 degrees to 90 degrees (e.g., FIG. 22), image processor 102 determines that the user is capturing an image of maxillary teeth and rotates image data to cause the tooth area to be below the gum area (S216). Meanwhile, if the value of cos γ is negative (No in S215), that is, angle γ ranges from 90 degrees to 180 degrees (e.g., FIG. 23), image processor 102 determines that the user is capturing an image of mandibular teeth and rotates the image data to cause the tooth area to be above the gum area (S217). For instance, as illustrated in FIG. 21, the image data is rotated to cause the tooth area to be above the gum area.

After step S216 or S217, image processor 102 rotates the image data according to the orientation of display 103 (the orientation of portable terminal 70) (S221). Then, image processor 102 horizontally flips the image data (S222).

Thus, if angle α is close to 45 degrees, image processor 102 determines the imaging direction (whether an image of the side surfaces of teeth or an image of the tops of teeth is captured), according to the relationship between the gum area and the tooth area and determines whether an imaging object is maxillary or mandibular according to the value of cos γ. This can improve the determination accuracy of image processor 102 when angle α is close to 45 degrees.

Variation 3

For instance, the above-mentioned determination of, for example, the direction in which a tooth image is captured, which is based on the orientation of intraoral camera 10 is performed on the assumption that the user who is, for example, standing upright or sitting in a chair faces forward. Meanwhile, when, for example, a dentist captures an image of patient's teeth, the image may be captured in a state in which a user (patient) lies face upward. In such a case, the relationship between the vertical axis and the teeth differs from that in a state in which the user faces forward. Thus, determination may not be performed properly. Hereinafter, a method that enables proper determination even in such a case is described.

Figure 24:
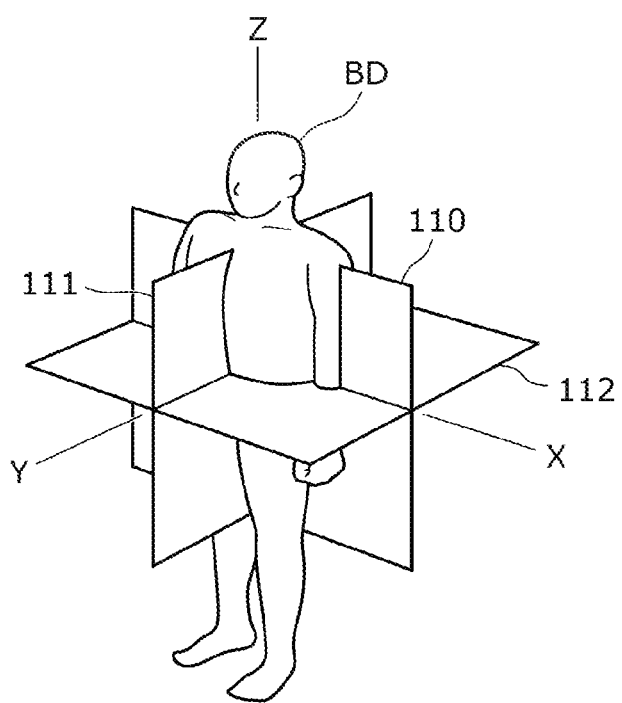
FIG. 24 illustrates relationships between projective planes and a standing user, according to Variation 3 of the embodiment.

FIG. 24 illustrates relationships between projective planes and standing user BD. Here, the projective planes are virtual planes relative to user BD and include the three planes: frontal plane 110, sagittal plane 111, and transverse plane 112. Frontal plane 110 divides the body of user BD into anterior and posterior halves and is perpendicular to a floor surface. Sagittal plane 111 passes through the body of user BD from front to back and divides the body of user BD into right and left halves. Sagittal plane 111 is perpendicular to the floor surface. Transverse plane 112 is parallel to the floor surface and divides the body of user BD into superior (upper) and inferior (lower) halves. Transverse plane 112 is perpendicular to both frontal plane 110 and sagittal plane 111.

In addition, axes of motion are a vertical axis, a sagittal-transverse axis, and a frontal-transverse axis. The x-axis in FIG. 24 is the frontal-transverse axis. The frontal-transverse axis is an axis in a left-right (horizontal) direction and the rotational axis of motions such as forward backward bend and flexion and extension on sagittal plane 111. The y-axis in FIG. 24 is the sagittal-transverse axis. The sagittal-transverse axis is an axis in an anteroposterior direction and is the rotational axis of motions such as side bend and abduction and adduction on frontal plane 110. The z-axis in FIG. 24 is the vertical axis. The vertical axis is an axis in a vertical direction and the rotational axis of motion such as rotational motion on transverse plane 112.

Figure 25:
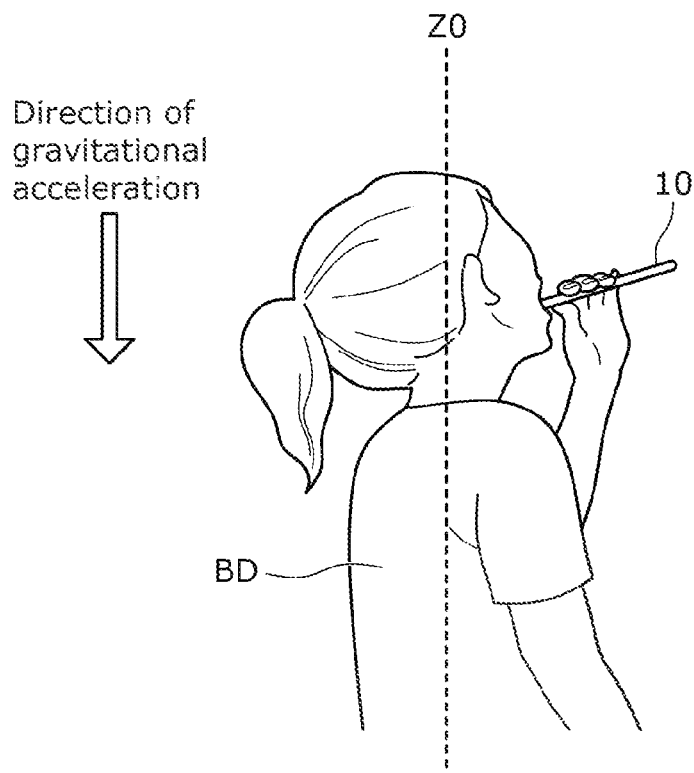
FIG. 25 illustrates an example of a user's posture during use of an intraoral camera, according to Variation 3 of the embodiment.
Figure 26:
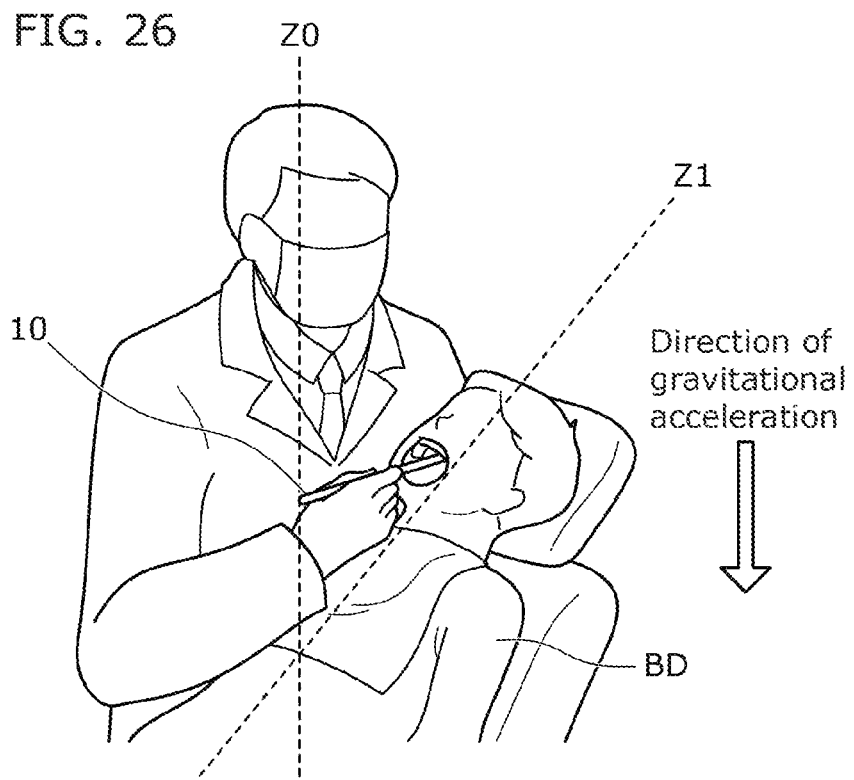
FIG. 26 illustrates an example of a user's posture during use of the intraoral camera, according to Variation 3 of the embodiment.

FIGS. 25 and 26 each illustrate an example of the posture of user BD during use of intraoral camera 10.

As illustrated in FIG. 25, when user BD standing upright or sitting in a chair uses intraoral camera 10, it is possible to assume that the user is standing. At this time, vertical axis Z0 of the body of user BD (the z-axis) is perpendicular to the floor surface and identical to the direction in which gravitational acceleration acts.

Meanwhile, as illustrated in FIG. 26, when for instance a dentist uses intraoral camera 10 for user BD lying on a dental chair, frontal plane 110 of the upper body of user BD is tilted parallel to the back of the dental chair. That is, since frontal plane 110 of user BD is tilted, vertical axis Z1 of the user whose upper body is tilted parallel to the back of the dental chair tilts relative to vertical axis Z0 of the body of user BD standing upright.

Figure 27:
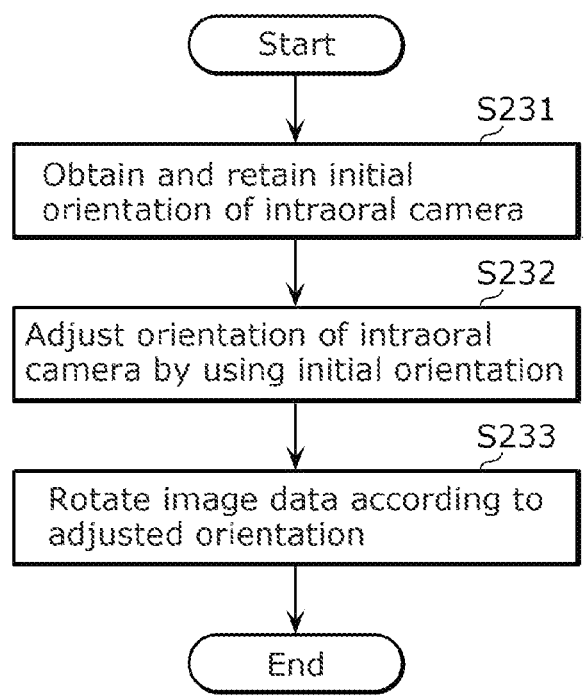
FIG. 27 is a flowchart illustrating image processing according to Variation 3 of the embodiment.
Figure 28:
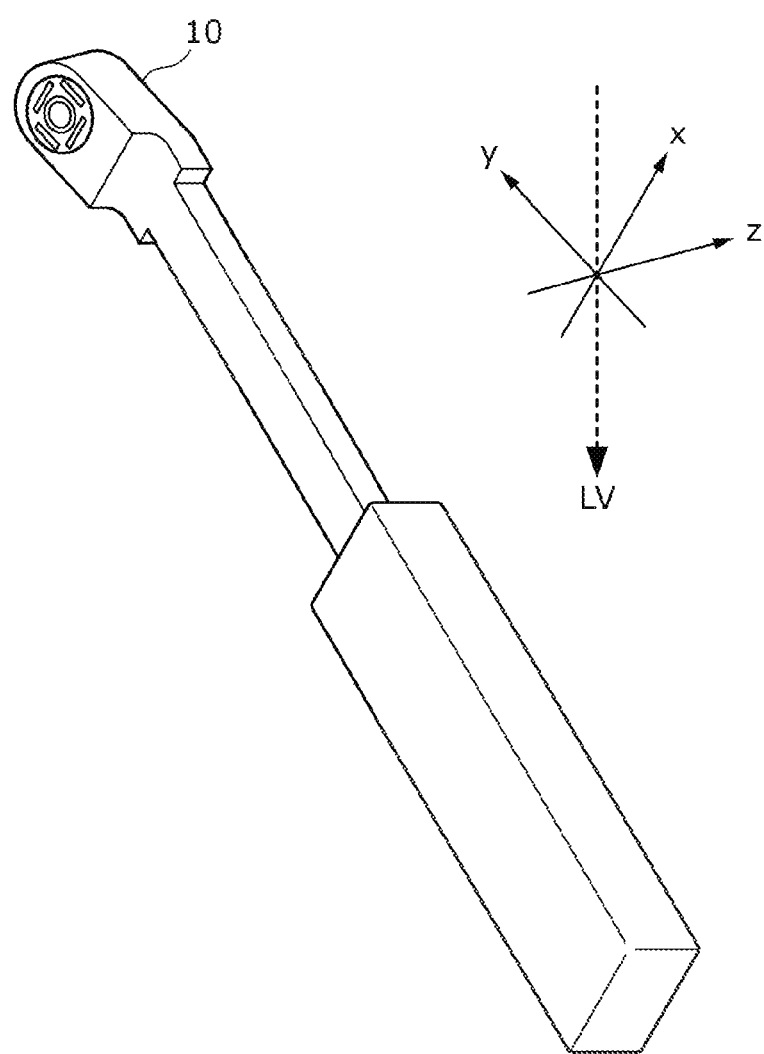
FIG. 28 illustrates an example of an initial orientation according to Variation 3 of the embodiment.

FIG. 27 is a flowchart illustrating image processing performed by image processor 102 when the posture of user BD changes in this manner. First, image processor 102 obtains and retains the initial orientation of intraoral camera 10 (S231). Specifically, on the basis of a user operation, image processor 102 obtains, as the initial orientation, the orientation of intraoral camera 10 when the user operation was performed. For instance, the initial orientation is obtained on the basis of a user operation for portable terminal 70. Alternatively, the initial orientation is obtained when, for example, a button provided on intraoral camera 10 is pressed. FIG. 28 illustrates an example of the initial orientation. For instance, as illustrated in FIG. 28, orientation information on three axes relative to vertical direction LV, obtained by position sensor 90 that is a six-axis sensor is obtained as the initial orientation. Portable terminal 70 or intraoral camera 10 retains the initial orientation.

Figure 29:
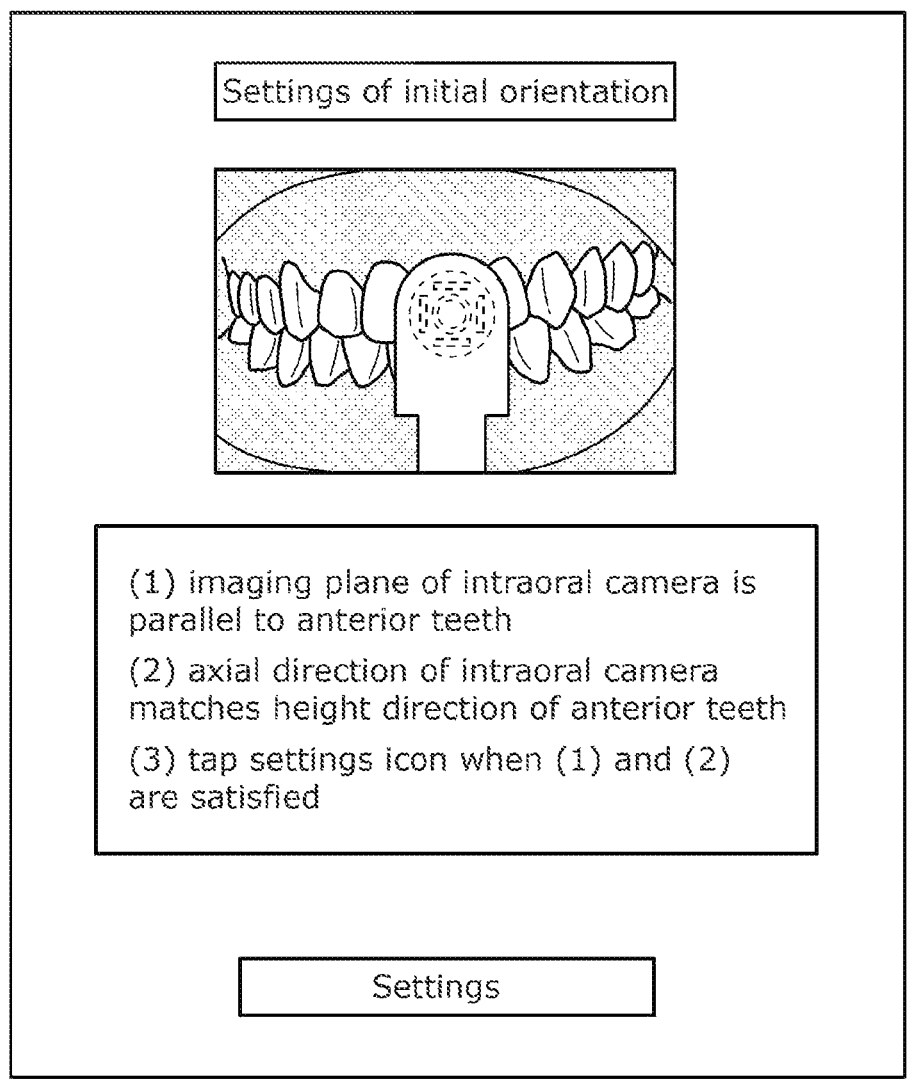
FIG. 29 illustrates an example of a setting screen to set the initial orientation according to Variation 3 of the embodiment.

FIG. 29 illustrates an example of an initial-orientation setting screen on portable terminal 70. As illustrated in FIG. 29, for instance, the orientation of intraoral camera 10 when teeth and intraoral camera 10 have a predetermined relationship is obtained as the initial orientation. In the initial orientation described in the example illustrated in FIG. 29, imaging plane S of intraoral camera 10 is parallel to the front surfaces of anterior teeth, and axial direction LB of intraoral camera 10 and a height direction of the anterior teeth are identical when viewed in the direction perpendicular to imaging plane S. It should be noted that a state in which the initial orientation is obtained is not limited to the above example and may be a given state based on at least one tooth. For instance, one or more teeth other than the anterior teeth may be used. In addition, part of the state specified above is the state in which axial direction LB of intraoral camera 10 matches the height (longitudinal) direction of the anterior teeth. However, a state in which axial direction LB of intraoral camera 10 is orthogonal to the height direction of the anterior teeth (a state in which the axis direction of intraoral camera 10 matches the width (lateral) direction of the anterior teeth) may be used.

In addition, the expressions: parallel, identical (match), and orthogonal described here are not limited to a perfectly parallel state, a perfectly identical state (perfect matching), and a perfectly orthogonal state. A substantially parallel state, a substantially identical state, and a substantially orthogonal state may be included. In other words, portable terminal 70 may instruct the user to achieve the above state, and the state used in the initial orientation may be the orientation of intraoral camera 10 achieved by the user in accordance with the instruction.

Figure 30:
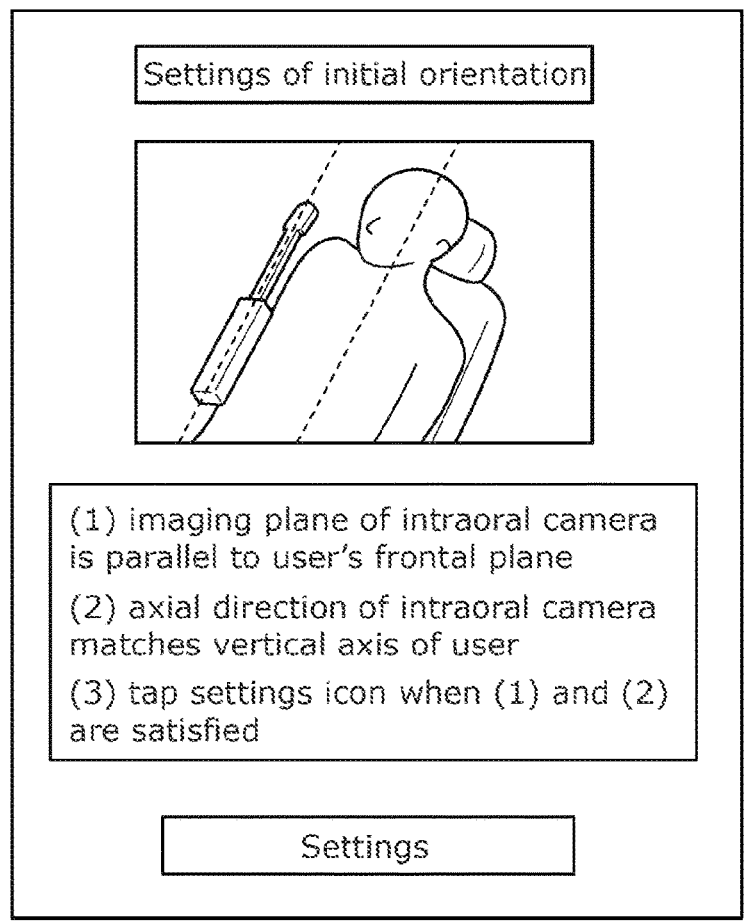
FIG. 30 illustrates an example of a setting screen to set the initial orientation according to Variation 3 of the embodiment.

FIG. 30 illustrates another example of the initial-orientation setting screen on portable terminal 70. As illustrated in FIG. 30, for instance, the orientation of intraoral camera 10 when the posture of the user and the orientation of intraoral camera 10 have a predetermined relationship is obtained as the initial state. In the initial orientation described in the example illustrated in FIG. 30, imaging plane S of the imaging unit is parallel to frontal plane 110 of user BD, and vertical axis Z1 of user BD and second direction LB are identical when viewed in the direction perpendicular to imaging plane S.

It should be noted that the state in which the initial orientation is obtained is not limited to the above example. A given orientation in which the posture of user BD can be associated with the orientation of intraoral camera 10 may be used. In addition, the posture of user BD may be defined using one or more of frontal plane 110, sagittal plane 111, transverse plane 112, the vertical axis, the sagittal-transverse axis, and the frontal-transverse axis. For instance, part of the state specified above is the state in which axial direction LB of intraoral camera 10 matches vertical axis Z1. However, a state in which axial direction LB of intraoral camera 10 is orthogonal to vertical axis Z1 (a state in which axial direction LB matches the frontal-transverse axis) may be used.

Next, capturing of a tooth image described above is performed. Specifically, image processor 102 adjusts the orientation of intraoral camera 10 obtained when the tooth image was captured, by using the initial orientation (S232). That is, by using the initial orientation, image processor 102 adjusts the orientation of intraoral camera 10 to be the orientation of intraoral camera 10 when the user faces forward.

Figure 31:
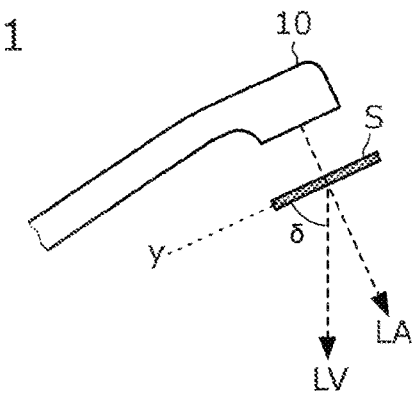
FIG. 31 illustrates an example of the initial orientation according to Variation 3 of the embodiment.
Figure 32:
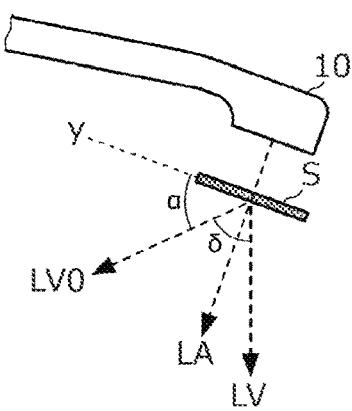
FIG. 32 illustrates an example of adjustment of the orientation according to Variation 3 of the embodiment.

FIG. 31 illustrates an example of the initial orientation. FIG. 32 illustrates an example of adjustment of the orientation. It should be noted that information on the y-axis is adjusted in the following example. However, the same applies to cases in which information on other axes is adjusted. As illustrated in FIG. 31, if angle δ formed by vertical direction LV and the y-axis is obtained as the initial orientation, image processor 102 adjusts vertical direction LV to be vertical direction LV0 as illustrated in FIG. 32. Vertical direction LV0 obtained after the adjustment is used instead of vertical direction LV when, for instance, imaging-direction determination processing is performed. For instance, as illustrated in FIG. 32, an angle formed by vertical direction LV0, which is the direction after the adjustment, and imaging plane S is calculated as angle α.

It should be noted that instead of adjusting vertical direction LV, image processor 102 may adjust the orientation itself obtained by position sensor 90 or a value being calculated (e.g., angle also used in determination). In addition, part or all of the adjustment processing may be performed by image processor 102 (portable terminal 70) or intraoral camera 10.

Finally, image processor 102 performs processing such as rotation of the image data according to the adjusted orientation (S233). Specifically, image processor 102 performs processing illustrated in FIG. 5, 14, 16, or 19, by using the adjusted orientation.

In this manner, image processor 102 can improve determination accuracy by adjusting the orientation of intraoral camera 10 according to the user's posture.

Thus, as illustrated in, for example, FIGS. 1, 2, and 4, the intraoral camera system includes the imaging unit (e.g., intraoral camera 10), position sensor 90, image processor 102, and display 103. The imaging unit (e.g., intraoral camera 10) includes handle 10b, head 10a, and neck 10c and captures an image of a tooth inside a mouth to generate image data, head 10a including an image sensor that generates the image data, and neck 10c connecting handle 10b to head 10a. Position sensor 90 detects the orientation of the imaging unit (e.g., intraoral camera 10). Image processor 102 performs image processing for the image data according to the orientation of the imaging unit (e.g., intraoral camera 10) detected by position sensor 90. Display 103 displays the image data that has undergone the image processing. For instance, as illustrated in, for example, FIGS. 5 to 13C, if first angle α formed by imaging plane S perpendicular to optical axis LA of the imaging unit (e.g., intraoral camera 10) and first direction LV (or LS) that is the vertically upward direction along the vertical axis is less than the predetermined second angle (e.g., 45 degrees) (Yes in S151), image processor 102 rotates the image data to cause the vertically upward direction along the vertical axis to coincide with the upward direction of the image by rotating the image data by third angle θ formed by first direction LS and second direction LB from handle 10b toward head 10a (S152).

Thus, the intraoral camera system can properly display the captured tooth image. For instance, the user can check the image reflecting the real vertical positional relationship. Accordingly, the user can intuitively understand their tooth condition.

For instance, as illustrated in, for example, FIGS. 5 to 13C, if first angle α is greater than or equal to the second angle (e.g., 45 degrees), image processor 102 rotates the image data to cause a portion of the image data corresponding to the head side of the imaging unit to appear at a top portion of the image (S153).

For instance, as illustrated in, for example, FIGS. 16 to 18, if first angle α is less than the second angle (e.g., 45 degrees) (Yes in S201), image processor 102 displays, on display 103, information notifying that the image being displayed on display 103 is an image of the side surface of a tooth captured inside a user's mouth by the imaging unit (e.g., intraoral camera 10) (S202). If first angle α is greater than or equal to the second angle (e.g., 45 degrees) (No in S201), image processor 102 displays, on display 103, information notifying that the image being displayed on display 103 is an image of the top of a tooth captured inside the user's mouth by the imaging unit (e.g., intraoral camera 10) (S203).

Thus, the intraoral camera system displays the direction in which a tooth image is captured. This enables the user to readily identify the direction in which the tooth image is currently being captured, which can improve user convenience.

For instance, as illustrated in, for example, FIGS. 19 to FIG. 23, if a difference between first angle α and the second angle (e.g., 45 degrees) is less than a predetermined value (Yes in S211), image processor 102 detects, from the image data, a tooth area and a gum area extending along the tooth area (S212). If the gum area is detected on both the buccal side and the lingual side of the tooth area (Yes in S213), image processor 102 rotates the image data to cause a portion of the image data corresponding to head 10a side of the imaging unit to appear at a top portion of the image (S220). If the gum area is detected only on one side of the buccal side and the lingual side of the tooth area (No in S213), image processor 102 calculates the cosine (cos γ) of fourth angle γ formed by first direction LS and the third direction that is the direction from the imaging unit toward a subject along optical axis LA of the imaging unit (S214). If the value of the calculated cosine is positive (Yes in S215), image processor 102 rotates the image data to cause the tooth area to be below the gum area in the image data (S216). If the value of the calculated cosine is negative (No in S215), image processor 102 rotates the image data to cause the tooth area to be above the gum area in the image data (S217).

Thus, if first angle α is close to the second angle (e.g., 45 degrees), the intraoral camera system rotates the image data according to the relationship between the gum area and the tooth area and the cosine (cos γ) of fourth angle γ. Thus, the intraoral camera system can improve determination accuracy when first angle α is close to the second angle (e.g., 45 degrees).

For instance, as illustrated in, for example, FIG. 5, image processor 102 further horizontally flips the image data, and display 103 displays the rotated and horizontally flipped image data (S155). This enables the user to check their teeth in the same state as their teeth are reflected on a mirror. Thus, the user can intuitively understand their tooth condition.

For instance, as illustrated in, for example, FIG. 5, image processor 102 further rotates the image data according to the orientation of display 103 (S154). Thus, for instance, the user can check the image reflecting the real vertical positional relationship. Accordingly, the user can intuitively understand their tooth condition.

For instance, as illustrated in FIGS. 24 to 32, image processor 102 obtains an initial orientation that is a predetermined orientation of the imaging unit (S231) and adjusts first direction LV (or LS) by using the initial orientation (S232).

Thus, the intraoral camera system can improve the accuracy of the processing by adjusting the orientation of the imaging unit according to the user's posture.

For instance, the predetermined orientation is the orientation of the imaging unit when the posture of user BD and the orientation of the imaging unit have a predetermined relationship.

For instance, in the predetermined orientation, imaging plane S of the imaging unit is parallel to frontal plane 110 of user BD, and vertical axis Z1 of user BD and second direction LB are identical or orthogonal when viewed in the direction perpendicular to imaging plane S.

For instance, in the predetermined orientation, a predetermined tooth (e.g., an anterior tooth) and imaging plane S of the imaging unit are parallel to and face each other, and second direction LB and a height direction of the predetermined tooth are identical or orthogonal when viewed in the direction perpendicular to imaging plane S.

Thus, the user can readily obtain the initial orientation. In addition, improvement in the accuracy of the initial orientation leads to improvement in the accuracy of adjustment.

The intraoral camera system according to the embodiment of the present disclosure is described above. However, the present disclosure is not limited to the descriptions in the embodiment.

For instance, in the example described above, intraoral camera 10 which is mainly used to capture a tooth image is used. However, intraoral camera 10 may be an intraoral care device including a camera. Intraoral camera 10 may be, for example, a dental washer including a camera.

In addition, the processing units included in the intraoral camera system according to the embodiment are typically embodied as LSIs, which are integrated circuits. The processing units may be made as individual chips, or a part or all of the processing units may be incorporated into one chip.

In addition, circuit integration may be achieved not only by an LSI but also by a dedicated circuit or a general-purpose processor. A field programmable gate array (FPGA), which is an LSI that can be programmed after manufacturing or a reconfigurable processor in which the connections and settings of circuit cells inside an LSI are reconfigurable may be used.

In addition, in the embodiment, each of the structural elements may be dedicated hardware or may be caused to function by running a software program suitable to the structural element. The structural element may be caused to function by a program running unit, such as a CPU or a processor, reading and running a software program stored in a recording medium, such as a hard disk or semiconductor memory.

In addition, the present disclosure may be achieved as, for example, an image display method implemented by the intraoral camera system. In addition, the present disclosure may be embodied as an intraoral camera, a portable terminal, or a cloud server included in the intraoral camera system.

In addition, the configuration of the functional blocks illustrated in the block diagram is a mere example. Two or more functional blocks may be incorporated into one functional block. One functional block may be divided into more than one functional block. A part of the function may be transferred from one functional block to another functional block. The same hardware or software may process the functions of two or more functional blocks having similar functions in parallel or on a time-sharing basis.

The order in which the steps are performed in each flowchart is provided as an example to specifically explain the present disclosure. The steps may be performed in a different order. In addition, a part of the steps and another step may be performed simultaneously (in parallel).

The intraoral camera system and the image display method according to one or more aspects are described above on the basis of the embodiment. However, the present disclosure is not limited to the embodiment. Within the scope of the present disclosure, one or more aspects may include one or more embodiments obtained by making various changes envisioned by those skilled in the art to the embodiment and one or more embodiments obtained by combining structural elements in different embodiments.

INDUSTRIAL APPLICABILITY

The present disclosure can be used in an intraoral camera system.

The invention claimed is:

1. An intraoral camera system comprising:
an imaging unit that includes a handle, a head, and a neck and captures an image of a tooth inside a mouth to generate image data, the head including an image sensor that generates the image data, and the neck connecting the handle to the head;
a sensor that detects an orientation of the imaging unit;
an image processor that performs image processing for the image data according to the orientation of the imaging unit detected by the sensor; and
a display that displays the image data that has undergone the image processing,
wherein if a first angle formed by an imaging plane perpendicular to an optical axis of the imaging unit and a first direction that is a vertically upward direction along a vertical axis is less than a predetermined second angle,
the image processor rotates the image data to cause the vertically upward direction along the vertical axis to coincide with an upward direction of an image by rotating the image data by a third angle formed by the first direction and a second direction from the handle toward the head.

2. The intraoral camera system according to claim 1, wherein if the first angle is greater than or equal to the second angle, the image processor rotates the image data to cause a portion of the image data corresponding to a head side of the imaging unit to appear at a top portion of an image.

3. The intraoral camera system according to claim 1, wherein if the first angle is less than the second angle, the image processor displays, on the display, information notifying that an image being displayed on the display is an image of a side surface of a tooth captured inside a mouth of a user by the imaging unit, and
if the first angle is greater than or equal to the second angle, the image processor displays, on the display, information notifying that an image being displayed on the display is an image of a top of a tooth captured inside the mouth of the user by the imaging unit.

4. The intraoral camera system according to claim 1, wherein if a difference between the first angle and the second angle is less than a predetermined value, the image processor detects, from the image data, a tooth area and a gum area extending along the tooth area,
if the gum area is detected on both a buccal side and a lingual side of the tooth area, the image processor rotates the image data to cause a portion of the image data corresponding to a head side of the imaging unit to appear at a top portion of an image, and
if the gum area is detected only on one of the buccal side and the lingual side of the tooth area, the image processor calculates a cosine of a fourth angle formed by the first direction and a third direction that is a direction from the imaging unit toward a subject along the optical axis of the imaging unit,
if a value of the cosine calculated is positive, the image processor rotates the image data to cause the tooth area to be below the gum area in the image data, and
if the value of the cosine calculated is negative, the image processor rotates the image data to cause the tooth area to be above the gum area in the image data.

5. The intraoral camera system according to claim 1, wherein the image processor further horizontally flips the image data, and
the display displays the image data that has been rotated and horizontally flipped.

6. The intraoral camera system according to claim 1, wherein the image processor further rotates the image data according to an orientation of the display.

7. The intraoral camera system according to claim 1, wherein the intraoral camera system obtains an initial orientation that is a predetermined orientation of the imaging unit and adjusts the first direction by using the initial orientation.

8. The intraoral camera system according to claim 7, wherein the predetermined orientation is an orientation of the imaging unit when a posture of a user and the orientation of the imaging unit have a predetermined relationship.

9. The intraoral camera system according to claim 8, wherein in the predetermined orientation, the imaging plane of the imaging unit is parallel to a frontal plane of the user, and a vertical axis of the user and the second direction are identical or orthogonal when viewed in a direction perpendicular to the imaging plane.

10. The intraoral camera system according to claim 7, wherein in the predetermined orientation, a predetermined tooth and the imaging plane of the imaging unit are parallel to and face each other, and the second direction and a height direction of the predetermined tooth are identical or orthogonal when viewed in a direction perpendicular to the imaging plane.

11. An image display method comprising:
capturing an image of a tooth inside a mouth to generate image data by an imaging unit that includes a handle, a head including an image sensor that generates the image data, and a neck connecting the handle to the head;
detecting an orientation of the imaging unit;
performing image processing for the image data according to the orientation of the imaging unit detected; and
displaying the image data that has undergone the image processing,
wherein in the image processing,
if a first angle formed by an imaging plane perpendicular to an optical axis of the imaging unit and a first direction that is a vertically upward direction along a vertical axis is less than a predetermined second angle,
by rotating the image data by a third angle formed by the first direction and a second direction from the handle toward the head, the image data is rotated to cause the vertically upward direction along the vertical axis to coincide with an upward direction of an image.

* * * * *